United States Patent [19]

Gassner et al.

[11] Patent Number: 5,011,849

[45] Date of Patent: Apr. 30, 1991

[54] COMPOUNDS FOR TREATING AND PREVENTING COGNITIVE DISEASES AND DEPRESSION AND METHODS OF MAKING SAME

[75] Inventors: Walter Gassner, Bottmingen; René Imhof, Gipf-Oberfrick; Emilio Kyburz, Reinach, all of Switzerland

[73] Assignee: Hoffmann-La Roche Inc., Nutley, N.J.

[21] Appl. No.: 383,777

[22] Filed: Jul. 21, 1989

[30] Foreign Application Priority Data

Jul. 28, 1988 [CH] Switzerland ............... 2871/88

[51] Int. Cl.$^5$ ............... C07D 277/56; C07D 263/40; C07D 233/90; A61K 31/425

[52] U.S. Cl. ............... 514/365; 514/370; 514/374; 514/377; 514/378; 514/380; 514/406; 514/407; 548/188; 548/194; 548/204; 548/233; 548/236; 548/246; 548/248; 548/378

[58] Field of Search ............... 548/188, 204, 194, 233, 548/236, 246, 248, 378; 514/365, 370, 374, 377, 378, 380, 406, 407

[56] References Cited

U.S. PATENT DOCUMENTS 4,764,522  8/1988  Imhof ............... 514/354

OTHER PUBLICATIONS

Kyburz E., "New Developments in the Field of Monoamine Oxidase Inhibitors", *Trends in Medicinal Chemistry*, 1988, H. van der Goot et al. (Editors), (Elsevier, Amsterdam 1989).

*Primary Examiner*—Robert Gerstl

*Attorney, Agent, or Firm*—George M. Gould; Bernard S. Leon; George W. Johnston

[57] ABSTRACT

Ethylenediamine monoamides of the formula $$R-CO-NH-CH_2-CH_2-NH_2 \qquad I$$

wherein R is one of groups

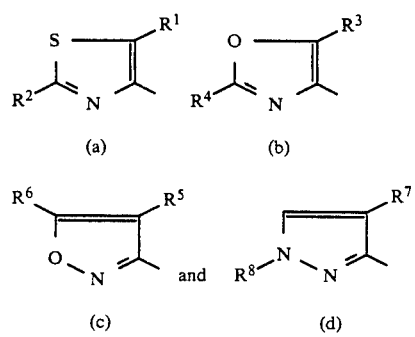

in which $R^1$ is phenyl monohalophenyl, monolower-alkylphenyl, monolower-alkoxypheynl, monotrifluoromethylphenyl, monocyanophenyl or monoaryl-lower-alkoxyphenyl, dihalophenyl, furyl, thienyl or monohalothienyl, $R^2$ is hydrogen, halogen or amino, $R^3$, $R^5$ and $R^7$ each are phenyl, monohalophenyl, dihalophenyl, thienyl, furyl or monohalofuryl, $R^4$ and $R^6$ each are hydrogen or amino and $R^8$ is hydrogen or lower-alkyl, as well as their pharmaceutically usable acid addition salts are disclosed. The compounds have monoamine oxidase inhibiting properties with low toxicity and are useful for the treatment of depressive states and cognitive disorders.

13 Claims, No Drawings

COMPOUNDS FOR TREATING AND PREVENTING COGNITIVE DISEASES AND DEPRESSION AND METHODS OF MAKING SAME

FIELD OF THE INVENTION

The present invention is concerned with ethylenediamine monoamide derivatives useful for preventing and treating depressive states and cognitive disorders.

SUMMARY OF THE INVENTION

In particular, the invention is concerned with ethylenediamine monoamides of the formula $$R—CO—NH—CH_2—CH_2—NH_2 \qquad I$$

wherein R is one of the groups

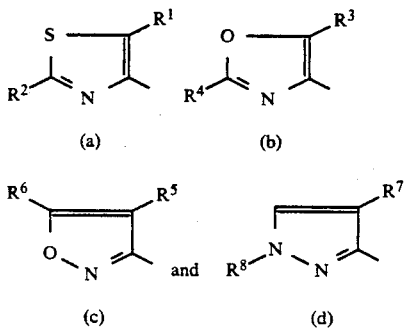

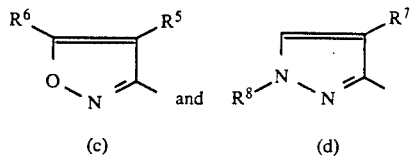

in which $R^1$ is phenyl, monohalophenyl, monolower-alkylphenyl, monolower-alkoxyphenyl, monotrifluoromethylphenyl, monocyanophenyl or monoaryl-lower-alkoxyphenyl, dihalophenyl, furyl, thienyl or monohalothienyl, $R^2$ is hydrogen, halogen or amino, $R^3$, $R^5$ and $R^7$ each are phenyl, monohalophenyl, dihalophenyl, thienyl, furyl or monohalofuryl, $R^4$ and $R^6$ each are hydrogen or amino and $R^8$ is hydrogen or lower-alkyl, as well as pharmaceutically usable acid addition salts thereof.

In the scope of the present invention it has surprisingly been found that the compounds of formula I have interesting and therapeutically valuable pharmacodynamic properties paired with low toxicity. In animal experiments it was shown that compounds of formula I above as well as their pharmaceutically acceptable acid addition salts possess monoamine oxidase (MAO) inhibiting properties. The novel compounds are thus useful as agents in the prevention and treatment of depressive states and cognitive disorders.

Detailed Description of the Prepared Embodiments

The present invention is concerned with ethylenediamine monamides of the formula $$R—CO—NH—CH_2—CH_2—NH_2 \qquad I$$

wherein R is one of the groups

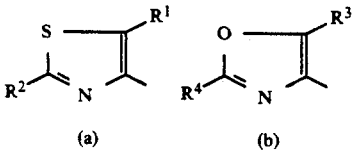

in which $R^1$ is phenyl monohalophenyl. monolower-alkylphenyl, monolower-alkoxyphenyl, monotrifluoromethylphenyl, monocyanophenyl or monoaryl-lower-alkoxyphenyl, dihalophenyl, furyl, thienyl or monohalothienyl, $R^2$ is hydrogen, halogen or amino, $R^3$, $R^5$ and $R^7$ each are phenyl, monohalophenyl, dihalophenyl, thienyl, furyl or monohalofuryl, $R^4$ and $R^6$ each are hydrogen or amino and $R^8$ is hydrogen or lower-alkyl, or a pharmaceutically acceptable acid addition salt of the compound of formula I.

The present invention relates to compounds of formula I as well as their pharmaceutically usable acid addition salts, and methods of using the compounds to treat depressive states and cognitive disorders. Medicaments containing a compound of formula I or a pharmaceutically usable acid addition salt thereof are also disclosed. Compounds of formula I. as well as their pharmaceutically usable acid addition salts, are useful in the control or prevention of illnesses or in the improvement of health, especially in the control or prevention of depressive states and cognitive disorders, especially of those which are caused by age. Finally, a process for the manufacture of the compounds of formula I above and of their pharmaceutically usable acid addition salts and compositions containing the compound of formula I, as well as the intermediates used in this process are objects of the present invention.

The term "lower-alkyl" used in this description relates to straight-chain and branched hydrocarbon residues with 1-3 carbon atoms, that is, methyl, ethyl, n-propyl an isopropyl.

The term "lower-alkoxy" relates to lower alkyl ether groups in which the term "lower-alkyl" has the above significance.

The term "aryl-lower-alkoxy" relates to lower alkyl ether groups in which one hydrogen atom is replaced by a phenyl residue which is optionally substituted by halogen, lower-alkyl, lower-alkoxy, nitro, cyano or hydroxy.

The term "halogen" embraces the four halogens fluorine, chlorine, bromine and iodine.

The term "leaving group" is in the scope of the present invention known groups such as halogen, preferably chlorine or bromine. Arylsulfonyloxy such as, for example, tosyloxy, alkylsulfonyloxy such as, for example, mesyloxy, and the like are also included.

The term "pharmaceutically usable or acceptable acid addition salts" embraces salts with inorganic and organic acids such as hydrochloric acid, hydrobromic acid, nitric acid, sulfuric acid, phosphoric acid, citric acid, formic acid, maleic acid, acetic acid, succinic acid, tartaric acid, methanesulfonic acid, p-toluenesulfonic acid and the like. Such salts can be prepared readily by a person skilled in the art and taking into consideration the nature of the compound to be converted into a salt.

preferred compounds of formula I are those in which R is group (a) or (b).

There are thus preferred those compounds in which R[1] is phenyl, monohalophenyl, monolower-alkylphenyl, monolower-alkoxyphenyl, monotrifluoromethylphenyl or mnonocyanophenyl, dihalophenyl, furyl, thienyl or monohalothienyl and R[2] is hydrogen or amino and those compounds in which R[3] is phenyl, monohalophenyl, dihalophenyl, thienyl, furyl or monohalofuryl, and R[4] is hydrogen.

Especially preferred are those compounds in which R[1] is phenyl, monohalophenyl or dihalophenyl and R[2] is hydrogen and those compounds in which R[3] is phenyl, monohalophenyl or dihalophenyl, and R[4] is hydrogen.

From the above it follows that of the compounds of formula I there are especially preferred those in which R is group (a) or (b), R[1] is phenyl, monohalophenyl or dihalophenyl and R[2] is hydrogen or R[3] is phenyl, monohalophenyl or dihalophenyl, and R[4] is hydrogen.

Particularly preferred compounds of formula I are:
N-(2-aminoethyl)-5-phenyl-4-thiazolecarboxamide
N-(2-aminoethyl)-5-(2-fluorophenyl)-4-thiazolecarboxamide
N-(2-aminoethyl)-5-(3-fluorophenyl)-4-thiazolecarboxamide
N-(2-aminoethyl)-5-(4-fluorophenyl)-4-thiazolecarboxamide
N-(2-aminoethyl)-5-(4-chlorophenyl)-4-oxazolecarboxamide
N-(2-aminoethyl)-5-(2-furyl)-4-oxazolecarboxamide
N-(2-aminoethyl)-5-(3,5-dichlorophenyl)-4-thiazolerboxamide
N-(2-aminoethyl)-5-(2,4-difluorophenyl)-4-thiazolecarboxamide
N-(2-aminoethyl)-5-(3,5-difluorophenyl)-4-thiazolecarboxamide
N-(2-aminoethyl)-5-(4-fluorophenyl)-4-oxazolecarboxamide
N-(2-aminoethyl)-5-(4-bromophenyl)-4-oxazolecarboxamide
N-(2-aminoethyl)-4-(3-fluorophenyl)-3-isoxazolecarboxamide and
N-(2-aminoethyl)-4-(3-fluorophenyl)-1-methyl-3-pyrazolecarboxamide.

The invention also relates to processes for making the compound of formula I and their corresponding acid addition salts. The compounds of formula I and their pharmaceutically usable acid addition salts can be prepared by (a) reacting a compound of the formula R—CO—OH  II wherein R has the above significance, in the form of the free acid or in the form of a reactive functional derivative thereof with ethylenediamine, or (b) reacting a compound of the formula R—CO—NH—CH$_2$—CH$_2$—R[9] 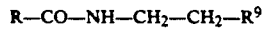 III wherein R has the above significance and R[9] is a leaving group, with ammonia, or (c) converting the residue R[10] in a compound of the formula R—CO—NH—CH$_2$—CH$_2$—R[10] 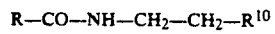 IV wherein R has the above significance and R[10] is a residue which is convertible into an amino group, into the amino group and, if desired, converting a compound obtained into a pharmaceutically usable acid addition salt.

As reactive functional derivatives of the acids of formula II there come into consideration, for example, halides, for example, chlorides, symmetrical or mixed anhydrides, esters, for example, methyl esters, p-nitrophenyl esters or N-hydroxysuccinimide esters, azides and amides, for example, imidazolides or succinimides.

The reaction of an acid of formula II or a reactive functional derivative thereof with ethylenediamine according to variant (a) of the above process can be carried out according to usual methods. Thus, for example, a free acid of formula II can be reacted with ethylenediamine in the presence of a condensation agent in an inert solvent. If a carbodiimide such as 1,1'-carbonyldiimidazole or dicyclohexylcarbodiimide is used as the condensation agent, then the reaction is conveniently carried out in an alkanecarboxylic acid ester such as ethyl acetate, an ether such as tetrahydrofuran or dioxan, a chlorinated hydrocarbon such as methylene chloride or chloroform, an aromatic hydrocarbon such as benzene, toluene or xylene, acetonitrile or dimethylformamide at a temperature between about 0° C. and about 100° C., preferably at about 60° C. If phosphorus trichloride is used as the condensation agent, then the reaction is conveniently carried out in a solvent such as pyridine at a temperature between about 0° C. and the reflux temperature of the reaction mixture. In another embodiment of variant (a), ethylenediamine is reacted with one of the above-mentioned reactive functional derivatives of an acid of formula II. Thus, for example, a halide, for example, the chloride, of an acid of formula II can be reacted at about 0° C. with ethylenediamine in the presence of a solvent such as for example, methylene chloride or ether.

The compounds of formula III are, for example, N-(2-haloethyl)carboxamides such as N-(2-chloroethyl)carboxamides, N-(2-methylsulfonylethyl)carboxamides or N-(2-p-toluenesulfonylethyl)carboxamides and the like.

In accordance with variant (b) a compound of formula III can be reacted with ammonia in a manner known per se at a temperature between about −40° C., and 50° C., if desired in the presence of a solvent such as dimethylformamide, dimethylacetamide, dimethyl sulfoxide and the like. The reaction is conveniently carried out in the presence of a solvent at about room temperature.

The conversion of the residue R[10] into amino in accordance with variant (c) is also effected in a manner known per se depending on the nature of the residue R[10]. If this is an amide, then the conversion is conveniently effected by acidic or basic hydrolysis. For the acidic hydrolysis there is advantageously used a solution of a mineral acid such as hydrochloric acid, aqueous hydrogen bromide, sulfuric acid, phosphoric acid and the like in an inert solvent such as an alcohol, for example, methanol or ethanol, an ether, for example, tetrahydrofuran or dioxan, and the like. For the basic hydrolysis there can be used aqueous solutions of alkali metal hydroxides such as potassium hydroxide solution or sodium hydroxide solution. Inert organic solvents such as those referred to above for the acidic hydrolysis can be added as solubilizers. The reaction temperature can be varied for the acidic and basic hydrolysis in a range from about room temperature to the reflux temperature. With the reaction being preferably carried out at the boiling temperature of the reaction mixture or slightly thereunder. If $R^{10}$ is phthalimido, then, in addition to the acidic and basic hydrolysis, an aminolysis with an aqueous solution of a lower alkylamine such as methylamine or ethylamine can also be carried out. A lower alkanol such as ethanol can be used as the organic solvent. The reaction is preferably carried out at room temperature. A third method for the conversion of phthalimido into amino comprises reacting compounds of formula IV with hydrazine in an inert solvent such as ethanol, a mixture of ethanol and chloroform, tetrahydrofuran or aqueous ethanol. The reaction temperature can be varied in a range from about room temperature up to about 100° C. with the reaction being preferably carried out at the boiling temperature of the chosen solvent. The resulting product can be extracted with dilute mineral acid and can subsequently be obtained by making the acidic solution basic. The t-butoxycarbonylamino residue is conveniently converted into the amino group with trifluoroacetic acid or formic acid in the presence or absence of an inert solvent such as methylene chloride at about room temperature, while the conversion of the trichloroethoxycarbonylamino group is effected with zinc or cadmium under acidic conditions. The acidic conditions are conveniently achieved by carrying out the reaction in acetic acid in the presence or absence of an additional inert solvent such as an alcohol, for example, methanol. The benzyloxycarbonylamino residue can be converted into the amino group in a known manner by acidic hydrolysis as described above or hydrogenolytically. An azido group can be reduced to the amino group according to known methods, for example with elementary hydrogen in the presence of a catalyst such as palladium/carbon, Raney-nickel, platinum oxide and the like. A hexamethylenetetraammonium group can be converted into the amino group by acidic hydrolysis according to likewise known methods.

The compounds of formula II and their reactive functional derivatives, which are used as starting materials in variant (a), are novel, but belong to known classes of substances and can be obtained in analogy to the preparation of known compounds. They are also an object of the present invention.

Processes for the preparation of in each case one type of compound of formula II in which R is group (a), (b), (c) or (d) are sketched in the following Schemes I and II in which $R^8$ is hydrogen or lower-alkyl and $R^{11}$ is hydrogen, halogen, lower-alkyl, lower-alkoxy, trifluoromethyl, cyano or aryl-lower-alkoxy. $R^{12}$ is lower-alkyl, $R^{13}$ is hydrogen or halogen and X is halogen. With respect to the specific reaction conditions, reference is made to the experimental part.

Scheme I

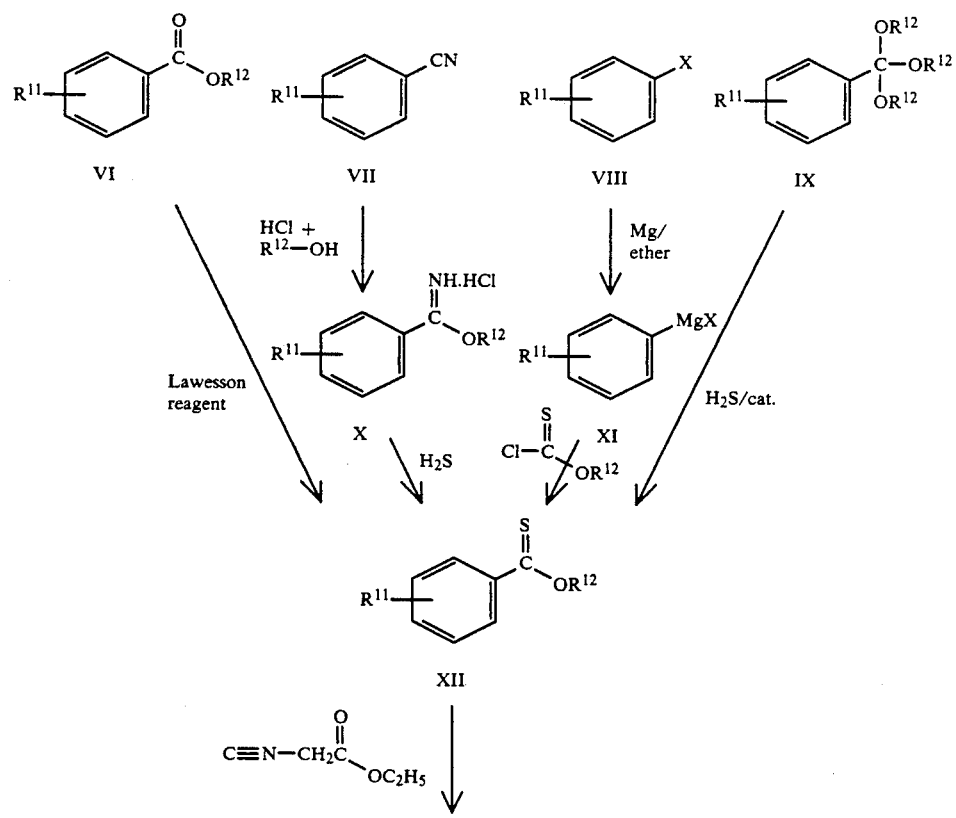

-continued
Scheme I
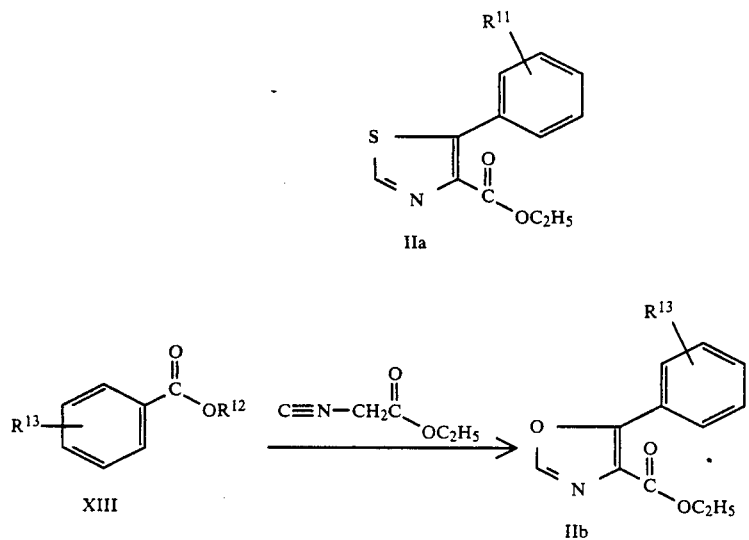
Scheme II
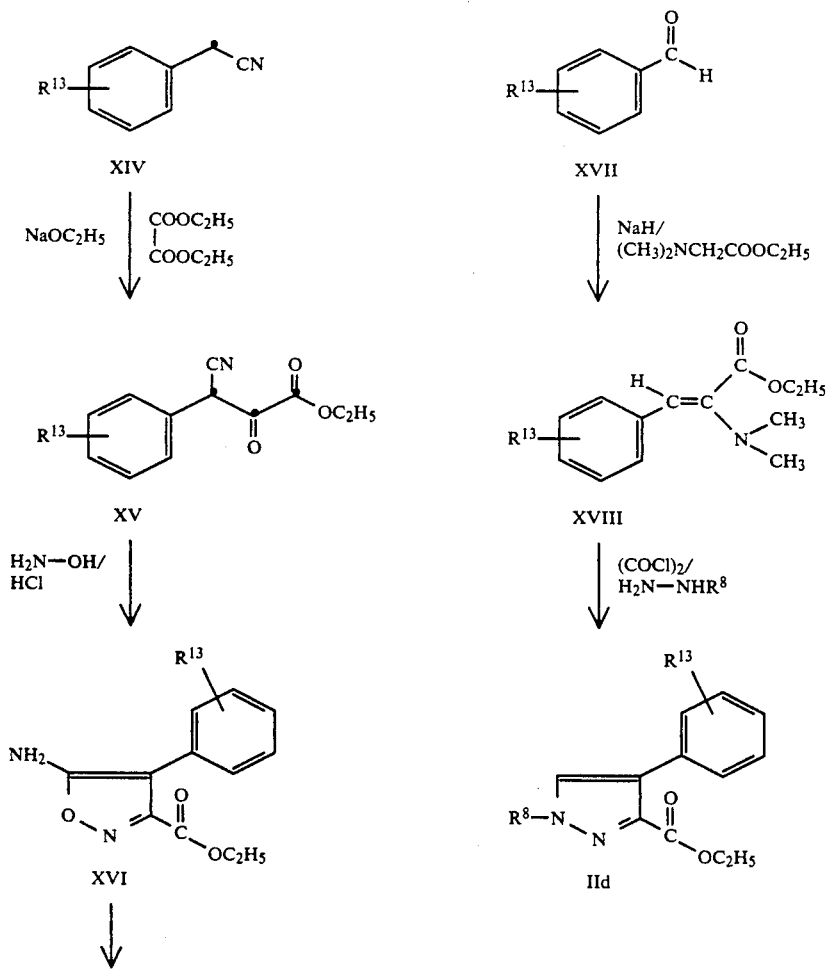

Scheme II

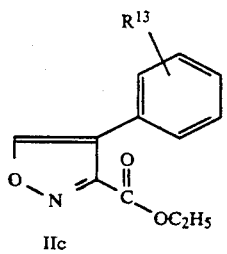

IIc

The compounds of formula III, which are used as starting materials in variant (b). are also novel, but again belong to known classes of substances and can be prepared in a manner known per se. They also form an object of the present invention. For example, a compound of formula II or a reactive functional derivative thereof can be reacted with ethanolamine under the reaction conditions given for variant (a) and the N-(2-hydroxyethyl)carboxamide obtained can be converted into the desired compound of formula III in a manner known per se, for example, by reaction with a halogenating agent such as phosphorus trichloride, phosphorus tribromide, phosphorus pentachloride, phosphorus oxychloride and the like, an arylsulfonyl halide such as tosyl chloride or an alkylsulfonyl halide such as mesyl chloride.

The compounds of formula IV. which are used as starting materials in variant c). are novel and are also an object of the present invention. They can be prepared in a manner known per se, for example by reacting a compound of formula II or a reactive functional derivative thereof with a compound of the formula

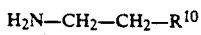

$H_2N-CH_2-CH_2-R^{10}$   V wherein $R^{10}$ has the above significance under the reaction conditions given for variant (a). The compounds of formula V are known or can be obtained in analogy to the preparation of the known compounds.

According to an alternative process the compounds of formula IV in which $R^{10}$ is phthalimido, azido or hexamethylenetetraammonium can also be obtained by reacting a compound of formula III with potassium phthalimide, an alkali metal azide or hexamethylenetetramine. The reaction is effected in a manner known per se under the reaction conditions given for variant (b).

As mentioned above, the compounds of formula I and their pharmaceutically usable acid addition salts have monoamine oxidase (MAO) inhibiting activity. On the basis of this activity the compounds of formula I and their pharmaceutically usable acid addition salts are useful for the treatment of depressive states and cognitive disorders, especially of those which are caused by age. Examples of such disorders are hypomnesis caused by age primary and secondary degenerative dementia, for example, dementia of the Alzheimer type or multi-infarct caused dementia, and cerebrovascular disorders and consequences of brain damages.

The MAO inhibiting activity of the compounds in accordance with the invention can be determined using standard methods. Thus, the preparations to be tested were subjected to the in vitro test described hereinafter, which followed the method published by R. J. Wurtmann and J. A. Axelrod [Biochem. Pharmac. 12, 1439–1441 (1963)].

Materials and Methods

Isolated rat brains are homogenized in the ratio 1:4 (weight/volume) in 0.1 molar potassium phosphate buffer (pH 7.4). whereupon the homogenates are diluted in the ratio 1:4 (volume/volume) with the same buffer and stored at $-20°$. A mixture of the following composition is used for the incubation:

100 $\mu l$ of 1M phosphate buffer (pH 7.4);
100 $\mu l$ solubilizate of the substance to be tested in water or dimethyl sulfoxide;
20 $\mu l$ of rat brain homogenate; and as the substrate
80 $\mu l$ of $^{14}C$-serotonin (5-HT) or $^{14}C$-phenylethylamine (PEA), in each case 100,000 decays per minute, corresponding to a final concentration of $2.10^{-4}$Mol/l and, respectively, $2.10^{-5}$Mol/l.

Prior to the addition of the substrate a preincubation at 37° C. was effected for 30 minutes. The incubation (in the presence of the substrate) was also effected at 37° C. and lasted 10 minutes.

The reaction is stopped by the addition of 200 $\mu l$ of 2N hydrochloric acid.

The deaminated product, depending on the use of 5-HT or of PEA as the substrate, is extracted by shaking for 10 minutes with 5 ml of diethyl ether or with 5 ml of n-heptane, whereupon the mixture is centrifuged, the aqueous phase is frozen in a dry-ice bath and the organic phase is poured into a counting glass.

The activity of the MAO in comparison to control homogenates (without substance to be tested) is determined on the basis of the $\beta$-counter value and the IC 50 is defined as that concentration of a substance to be tested which decreases the activity of the MAO in the substrate 5-HT or PEA to 50%.

The thus-determined activity of some compounds in accordance with the invention will be evident from the $IC_{50}$ values listed in Table 1 below:

TABLE I

| Compound | IC 50, $\mu$Mol/l | |
|---|---|---|
| "N-(2-Aminoethyl)-... carboxamide" | 5-HT | PEA |
| ... 5-phenyl-4-thiazol ... | 0.02 | 20 |
| ... 5-(2-fluorophenyl)-4-thiazol ... | 0.04 | >10 |
| ... 5-(3-fluorophenyl)-4-thiazol ... | 0.02 | >10 |
| ... 5-(4-fluorophenyl)-4-thiazol ... | 0.06 | 100 |
| ... 5-(4-chlorophenyl)-4-oxazol ... | <0.01 | >100 |
| ... 5-(2-furyl)-4-oxazol ... | 0.022 | 2.0 |
| ... 5-(3,5-dichlorophenyl)-4-thiazol ... | 0.007 | 0.3 |
| ... 5-(2,4-difluorophenyl)-4-thiazol ... | 0.12 | 3.6 |

Dosage Form

The compounds of formula I as well as their pharmaceutically usable acid addition salts can be used as medicaments, for example, in the form of pharmaceutical preparations including pharmaceutically acceptable carrier materials. The pharmaceutical preparations can be administered orally, for example, in the form of tablets, coated tablets, dragees, hard and soft gelatin capsules, solutions, emulsions or suspensions. The administration can, however, also be effected rectally, for example, in the form of suppositories, or parenterally, for example, in the form of injection solutions.

For the manufacture of tablets, coated tablets, dragees and hard gelatin capsules the compounds of formula I and their pharmaceutically usable acid addition salts can be processed with pharmaceutically acceptable carriers, such as inert, inorganic or organic excipients. Lactose, maize starch or derivatives thereof, talc, stearic acid or its salts etc. can be used as such excipients for, for example, tablets, dragees and hard gelatin capsules.

Suitable excipients for soft gelatin capsules are for example, vegetable oils, waxes, fats, semi-solid and liquid polyols etc.

Suitable excipients for the manufacture of solutions and syrups are for example, water, polyols, saccharose, invert sugar, glucose etc.

Suitable excipients for injection solutions are for example, water, alcohols, polyols, glycerine, vegetable oils etc.

Suitable excipients for suppositories are for example, natural or hardened oils, waxes, fats, semi-liquid or liquid polyols etc.

The pharmaceutical preparations can also contain preserving agents, solubilizers, stabilizing agents, wetting agents, emulsifying agents, sweetening agents, coloring agents, flavoring agents, salts for varying the osmotic pressure, buffers, coating agents or antioxidants. They can also contain other therapeutically valuable substances.

In accordance with the invention compounds of formula I as well as their pharmaceutically usable acid addition salts can be used in the control or prevention of depressive states and cognitive disorders, especially those which are caused by age. The dosage can vary within wide limits and will, of course, be fitted to the individual requirements in each particular case. In general, in the case of oral administration a daily dosage of about 50 to 500 mg, preferably of about 100 to 300 mg, of a compound of formula I should be appropriate, although the upper limit just mentioned can also be exceeded when this is shown to be indicated.

The following Examples illustrate the present invention but are not intended to limit its extent in any manner. While the examples describe what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

Unless otherwise stated, percentages and ratios relating to solvent mixtures are expressed in volume, purity data determined by gas chromatography are expressed in area %, and the remaining percentages and ratios are expressed in weight. Temperatures are in degrees Celsius (° C.). normal pressure is about 1 atmosphere, and room temperature is about 20° C. Examples were carried out as written unless otherwise indicated.

EXAMPLE 1

(A) 4.3 g (12.37 mmol) of t-butyl [2-(5-phenyl-4-thiazolecarboxamido)ethyl]carbamate were dissolved in 10 ml of methylene chloride, treated with 5.0 ml of trifluoro-acetic acid and stirred at 20° for 16 hours and at 60° for 1 hour. Subsequently, the mixture was concentrated under reduced pressure. The residue was dissolved in 10 ml of ethanol, treated with 3 ml of 17.5% (w/v) ethanolic hydro-chloric acid and evaporated. The residue was recrystallized from methanol, whereby 3.3 g (94%) of N-(2-aminoethyl)-5-phenyl-4-thiazolecarboxamide hydrochloride were obtained as white crystals, melting point 243°–245°.

The t-butyl [2-(5-phenyl-4-thiazolecarboxamido)ethyl]carbamate used as the starting material was prepared as follows:

(B) 70 ml (0.487 mol) of ethyl benzoate were heated to reflux for 12 hours with 100 g (0.247 mol) of Lawesson reagent in 350 ml of xylene. After cooling to 20° the reaction mixture was diluted with 500 ml of hexane and filtered. The filtrate was flash-chromatographed on 1 kg of silica gel. Elution was carried out with hexane. The fractions which were pure according to the thin-layer chromatogram (eluent: toluene) were combined and evaporated under reduced pressure. There were obtained 72 g (89%) of O-ethyl thiobenzoate as a dark yellow evil-smelling oil which was used without further purification.

(C) Analogously to the method described in Synthesis 10, (1976), 681–682, the O-ethyl thiobenzoate was converted with ethyl isocyanoacetate in the presence of 1–5% powdered potassium hydroxide in ethanol in 70% yield into ethyl 5-phenyl-4-thiazolecarboxylate which melted at 79°–80° after recrystallization from ethyl acetate/hexane.

(D) The ethyl 5-phenylthiazole-4-carboxylate was hydrolyzed according to known methods with 2N aqueous sodium hydroxide solution at 70° for 30 minutes, whereby, after acidification, there was obtained in 72% yield 5-phenyl-4-thiazolecarboxylic acid which melted at 189°–190° after recrystallization from methanol/diethyl ether.

(E) 4.03 g (24.85 mmol) of 1,1′-carbonyldiimidazole were added to a solution of 5.0 g (24.36 mmol) of 5-phenyl-4-thiazolecarboxylic acid in 100 ml of abs. tetrahydrofuran and the reaction mixture was stirred at 25° for 2 hours, whereby a $CO_2$-evolution occured.

Thereafter, 4.1 g (25.59 mmol) of t-butyl (2-aminoethyl)carbamate were added thereto. The reaction mixture was left to stir at 50° for 2 hours and was thereafter evaporated under reduced pressure. The oily residue was dissolved in methylene chloride and chromatographed on 50 g of silica gel. Elution was first carried out with methylene chloride, then with an 8:2 and 7:3 mixture of methylene chloride and ethyl acetate and finally with ethyl acetate. The fractions which were pure according to the thin-layer chromatogram (methylene chloride/ethyl acetate 7:3) were combined and recrystallized from ethyl acetate/hexane, whereby there were obtained 7.7 g (91%) of t-butyl [2-(5-phenyl-4-thiazolecarboxamido)ethyl]carbamate as white crystals, melting point 139°–140°.

(E1) 4.8 g (20.58 mmol) of ethyl 5-phenyl-4-thiazolecarboxylate and 4.0 g (25.0 mmol) of t-butyl (2-aminoethyl)carbamate were heated under reduced pressure for 21 hours at a bath temperature of 100°, whereby the ethanol formed was distilled off continuously. Subsequently the mixture was cooled, dissolved in 50 ml of methylene chloride and chromatographed on 150 g of silica gel. Elution was first carried out with methylene chloride, then with a 9:1, 8:2 and finally 7:3 mixture of methylene chloride and ethyl acetate. The fractions which were pure according to the thin-layer chromatogram were combined and recrystallized from ethyl acetate/hexane. In this manner there were obtained 4.3 g (60.1%) of t-butyl [2-(5-phenyl-4-thiazolecarboxamido)ethyl]carbamate as white crystals, melting point 139-140°.

(E2) 2.0 g (9.75 mmol) of 5-phenyl-4-thiazolecarboxylic acid were placed in 20 ml of chloroform with 0.8 g (10.4 mmol) of methyl chloroformate and cooled to 0°, 1.5 ml (10.8 mmol) of triethylamine were added dropwise thereto at 0°-5°. After stirring at 0°-5° for 30 minutes the reaction mixture was added dropwise within 1.5 hours to an ice-cooled solution of 1.6 g (10 mmol) of t-butyl (2-aminoethyl)carbamate in 20 ml of chloroform. The reaction mixture was stirred at 0°-5° for a further 30 minutes, subsequently diluted with 150 ml of methylene chloride and washed with in each case 100 ml of water, saturated sodium bicarbonate solution as well as sodium chloride solution. The aqueous phases were back-extracted with 100 ml of methylene chloride. The combined organic phases were dried over magnesium sulfate and evaporated. The crystalline residue was recrystallized from ethyl acetate/hexane, whereby there were obtained, after drying. 2.4 g (70.9%) of t-butyl [2-(5-phenyl-4-thiazolecarboxamido)ethyl]carbamate as white crystals, melting point 139°-140°.

EXAMPLE 2

The following compounds were prepared in an analogous manner to that described in Example 1(A):

From t-butyl [2-[5-(2-fluorophenyl)-4-thiazolecarboxamido]ethyl]carbamate the N-(2-aminoethyl)-5-(2-fluorophenyl)-4-thiazolecarboxamide hydrochloride in 95% yield, melting point 239°-240° (from methanol/diethyl ether);

from t-butyl [2-[5-(3-fluorophenyl)-4-thiazolecarboxamido]ethyl]carbamate the N-(2-aminoethyl)-5-(3-fluorophenyl)-4-thiazolecarboxamide hydrochloride in 90% yield, melting point 244°-246° (from methanol/diethyl ether);

from t-butyl [2-[5-(4-fluorophenyl)-4-thiazolecarboxamido]ethyl]carbamate the N-(2-aminoethyl)-5-(4-fluorophenyl)-4-thiazolecarboxamide hydrochloride in 90% yield, melting point 25820 -259° (from methanol/diethyl ether);

from t-butyl [2-[5-(2-chlorophenyl)-4-thiazolecarboxamido]ethyl]carbamate the N-(2-aminoethyl)-5-(2-chlorophenyl)-4-thiazolecarboxamide hydrochloride in 85% yield, melting point 264°-266° (from methanol/diethyl ether);

from t-butyl [2-[5-(3-chlorophenyl)-4-thiazolecarboxamido]ethyl]carbamate the N-(2-aminoethyl)-5-(3-chlorophenyl)-4-thiazolecarboxamide hydrochloride in 92% yield, melting point 257°-258° (from methanol/diethyl ether);

from t-butyl [2-[5-(4-chlorophenyl)-4-thiazolecarboxamido]ethyl]carbamate the N-(2-aminoethyl)-5-(4-chlorophenyl)-4-thiazolecarboxamide hydrochloride in 86% yield, melting point 272°-274° (from methanol/diethyl ether);

from t-butyl [2-[5-(3-bromophenyl)-4-thiazolecarboxamido]ethyl]carbamate the N-(2-aminoethyl)-5-(3-bromophenyl)-4-thiazolecarboxamide hydrochloride in 92% yield, melting point 260°-261° (from methanol/diethyl ether);

from t-butyl [2-[5-(3,5-dichlorophenyl)-4-thiazolecarboxamido]ethyl]carbamate the N-(2-aminoethyl)-5-(3,5-dichlorophenyl)-4-thiazolecarboxamide hydrochloride in 67% yield, melting point 294°-295° (from methanol);

from t-butyl [2-[5-(2-methylphenyl)-4-thiazolecarboxamido]ethyl]carbamate the N-(2-aminoethyl)-5-(2-methylphenyl)-4-thiazolecarboxamide hydrochloride in 80% yield, melting point 278°-279° (from methanol/diethyl ether):

from t-butyl [2-[5-(3-methylphenyl)-4-thiazolecarboxamido]ethyl]carbamate the N-(2-aminoethyl)-5-(3-methylphenyl)-4-thiazolecarboxamide hydrochloride in 89% yield, melting point 261°-262° (from methanol/diethyl ether);

from t-butyl [2-[5-(4-methylphenyl)-4-thiazolecarboxamido]ethyl]carbamate the N-(2-aminoethyl)-5-(4-methylphenyl)-4-thiazolecarboxamide hydrochloride in 91% yield, melting point 259°-261° (from methanol/diethyl ether);

from t-butyl [2-[5-(2-methoxyphenyl)-4-thiazolecarboxamido]ethyl]carbamate the N-(2-aminoethyl)-5-(2-methoxyphenyl)-4-thiazolecarboxamide hydrochloride in 84% yield, melting point 230°-231° (from methanol/diethyl ether);

from t-butyl [2-[5-(3-methoxyphenyl)-4-thiazolecarboxamido]ethyl]carbamate the N-(2-aminoethyl)-5--(3-methoxyphenyl)-4-thiazolecarboxamide hydrochloride in 82% yield, melting point 242°-243° (from methanol/diethyl ether):

from t-butyl [2-[5-(4-methoxyphenyl)-4-thiazolecarboxamido]ethyl]carbamate the N-(2-aminoethyl)-5-(4-methoxyphenyl)-4-thiazolecarboxamide hydrochloride in 82% yield, melting point 263°-265° (from methanol/diethyl ether);

from t-butyl [2-[5-($\alpha,\alpha,\alpha$-trifluoro-3-methylphenyl)-4-thiazolecarboxamido]ethyl]carbamate the N-(2-aminoethyl)-5-($\alpha,\alpha,\alpha$-trifluoro-3-methylphenyl)-4-thiazolecarboxamide hydrochloride in 86% yield, melting point 226°-227° (from ethanol);

from t-butyl [2-[5-($\alpha,\alpha,\alpha$-trifluoro-4-methylphenyl)-4-thiazolecarboxamido]ethyl]carbamate the N-(2-aminoethyl)-5-($\alpha,\alpha,\alpha$-trifluoro-4-methylphenyl)-4-thiazolecarboxamide hydrochloride in 86% yield, melting point 281°-284° (from methanol/diethyl ether);

from t-butyl [2-[5-(3-cyanophenyl)-4-thiazolecarboxamido]ethyl]carbamate the N-(2-aminoethyl)-5-(3-cyanophenyl)-4-thiazolecarboxamide hydrochloride in 75% yield. melting point 244°-246° (from methanol/diethyl ether);

from t-butyl [2-[5-(4-cyanophenyl)-4-thiazolecarboxamido]ethyl]carbamate the N-(2-aminoethyl)-5-(4-cyanophenyl)-4-thiazolecarboxamide hydrochloride in 73% yield, melting point 250°-252° (from methanol);

from t-butyl [2-[5-(2,4-dichlorophenyl)-4-thiazolecarboxamido]ethyl]carbamate the N-(2-aminoethyl)-5-(2,4-dichlorophenyl)-4-thiazolecarboxamide hydrochloride in 86% yield, melting point 278°-280° (from methanol/diethyl ether);

from t-butyl [2-[5-(3,4-dichlorophenyl)-4-thiazolecarboxamido]ethyl]carbamate the N-(2-aminoethyl)-5-

(3,4-dichlorophenyl)-4-thiazolecarboxamide hydrochloride in 90% yield, melting point 244°-247° (from methanol/diethyl ether);

from t-butyl [2-[5-(2,4-difluorophenyl)-4-thiazolecarboxamido]ethyl]carbamate the N-(2-aminoethyl)-5-(2,4-difluorophenyl)-4-thiazolecarboxamide hydrochloride in 94% yield, melting point 269°-271° (from methanol);

from t-butyl [2-[5-(2-thienyl)-4-thiazolecarboxamido]ethyl]carbamate the N-(2-aminoethyl)-5-(2-thienyl)-4-thiazolecarboxamide hydrochloride in 93% yield, melting point 251°-254° (from methanol/diethyl ether);

from t-butyl [2-[5-(3-thienyl)-4-thiazolecarboxamido]ethyl]carbamate the N-(2-aminoethyl)-5-(3-thienyl)-4-thiazolecarboxamide hydrochloride in 89% yield, melting point 265°-266° (from methanol/diethyl ether);

from t-butyl [2-[5-(5-bromo-2-thienyl)-4-thiazolecarboxamido]ethyl]carbamate the N-(2-aminoethyl)-5-(5-bromo-2-thienyl)-4-thiazolecarboxamide hydrochloride in 77% yield, melting point 267°-269° (from methanol/diethyl ether);

from t-butyl [2-[5-(2-furyl)-4-thiazolecarboxamido]ethyl]carbamate the N-(2-aminoethyl)-5-(2-furyl)-4-thiazolecarboxamide hydrochloride in 80% yield, melting point 254° (from methanol/diethyl ether);

from t-butyl [2-[5-(2,3-dichlorophenyl)-4-thiazolecarboxamido]ethyl]carbamate the N-(2-aminoethyl)-5-(2,3-dichlorophenyl)-4-thiazolecarboxamide hydrochloride in 96% yield, melting point 263°-265° (from methanol/diethyl ether);

from t-butyl [2-[5-(2,5-dichlorophenyl)-4-thiazolecarboxamido]ethyl]carbamate the N-(2-aminoethyl)-5-(2,5-dichlorophenyl)-4-thiazolecarboxamide hydrochloride in 80% yield, melting point 252°-253° (from methanol); and from t-butyl [2-[5-(3,4-difluorophenyl)-4-thiazolecarboxamido]ethyl]carbamate the N-(2-aminoethyl)-5-(3,4-difluorophenyl)-4-thiazolecarboxamide hydrochloride in 94% yield, melting point 242°-244° (from methanol/diethyl ether).

The above-mentioned carbamates used as the starting materials were prepared as follows:

The following carbamates were prepared in an analogous manner to that described in Example 1(E1):

From ethyl 5-(2-fluorophenyl)-4-thiazolecarboxylate and t-butyl (2-aminoethyl)carbamate the t-butyl [2-[5-(2-fluorophenyl)-4-thiazolecarboxamido]ethyl]carbamate in 59% yield, melting point 143° (from ethyl acetate/hexane);

from ethyl 5-(3-fluorophenyl)-4-thiazolecarboxylate and t-butyl (2-aminoethyl)carbamate the t-butyl [2-[5-(3-fluorophenyl)-4-thiazolecarboxamido]ethyl]carbamate in 60% yield, melting point 142°-143° (from ethyl acetate/hexane);

from ethyl 5-(4-fluorophenyl)-4-thiazolecarboxylate and t-butyl (2-aminoethyl)carbamate the t-butyl [2-[5-(4-fluorophenyl)-4-thiazolecarboxamido]ethyl]carbamate in 46% yield, melting point 110°-111° (from ethyl acetate/hexane);

from ethyl 5-(2-chlorophenyl)-4-thiazolecarboxylate and t-butyl (2-aminoethyl)carbamate the t-butyl [2-[5-(2-chlorophenyl)-4-thiazolecarboxamido]ethyl]carbamate in 68% yield, melting point 166°-167° (from ethyl acetate/hexane);

from ethyl 5-(3-chlorophenyl)-4-thiazolecarboxylate and t-butyl (2-aminoethyl)carbamate the t-butyl [2-[5-(3-chlorophenyl)-4-thiazolecarboxamido]ethyl]carbamate in 72% yield, melting point 122°-123° (from ethyl acetate/hexane);

from ethyl 5-(4-chlorophenyl)-4-thiazolecarboxylate and t-butyl (2-aminoethyl)carbamate the t-butyl [2-[5-(4-chlorophenyl)-4-thiazolecarboxamido]ethyl]carbamate in 63% yield, melting point 147°-148° (from ethyl acetate/hexane);

from ethyl 5-(3-bromophenyl)-4-thiazolecarboxylate and t-butyl (2-aminoethyl)carbamate the t-butyl [2-[5-(3-bromophenyl)-4-thiazolecarboxamido]ethyl]carbamate in 79% yield, melting point 124°-125° (from ethyl acetate/hexane);

from ethyl 5-(3,5-dichlorophenyl)-4-thiazolecarboxylate and t-butyl (2-aminoethyl)carbamate the t-butyl [2-[5-(3,5-dichlorophenyl)-4-thiazolecarboxamido]ethyl]carbamate in 42% yield, melting point 130-132° (from ethyl acetate/hexane);

from ethyl 5-(2-methylphenyl)-4-thiazolecarboxylate and t-butyl (2-aminoethyl)carbamate the t-butyl [2-[5-(2-methylphenyl)-4-thiazolecarboxamido]ethyl]carbamate in 44% yield, melting point 163-164° (from ethyl acetate/hexane);

from ethyl 5-(3-methylphenyl)-4-thiazolecarboxylate and t-butyl (2-aminoethyl) carbamate the t-butyl [2-[5-(3-methylphenyl)-4-thiazolecarboxamido]ethyl]carbamate in 35% yield, melting point 112°-113° (from ethyl acetate/hexane);

from ethyl 5-(4-methylphenyl)-4-thiazolecarboxylate and t-butyl (2-aminoethyl)carbamate the t-butyl [2-[5-(4-methylphenyl)-4-thiazolecarboxamido]ethyl]carbamate in 60% yield, melting point 133-134° (from ethyl acetate/hexane):

from ethyl 5-(2-methoxyphenyl)-4-thiazolecarboxylate and t-butyl (2-aminoethyl)carbamate the t-butyl [2-[5-(2-ethoxyphenyl)-4-thiazolecarboxamido]ethyl]carbamate in 17.5% yield, melting point 142°-143° (from ethyl acetate/hexane);

from ethyl 5-(3-methoxyphenyl)-4-thiazolecarboxylate and t-butyl (2-aminoethyl)carbamate the t-butyl [2-[5-(3-methoxypehnyl)4-thiazolecarboxamido]ethyl]carbamate in 66% yield, melting point 98°-100° (from ethyl acetate/hexane);

from ethyl 5-(4-methoxyphenyl)-4-thiazolecarboxylate and t-butyl (2-aminoethyl)carbamate the t-butyl [2-[5-(4methoxyphenyl)-4-thiazolecarboxamido]ethyl]carbamate in 61% yield, melting point 102° (from ethyl acetate/hexane);

from ethyl 5-($\alpha,\alpha,\alpha$-trifluoro-3-methylphenyl)-4-thiazolecarboxylate and t-butyl (2-aminoethyl)carbamate the t-butyl [2-[5-($\alpha,\alpha,\alpha$-trifluoro-3-methylphenyl)-4-thiazolecarboxamido[ethyl]carbamate in 24% yield, melting point 119°-120° (from ethyl acetate/hexane);

from ethyl 5-($\alpha,\alpha,\alpha$-trifluoro-4-methylphenyl)-4-thiazolecarboxylate and t-butyl (2-aminoethyl)carbamate the t-butyl [2-[5-($\alpha,\alpha,\alpha$-trifluoro-4-methylphenyl)-4-thiazolecarboxamido]ethyl]carbamate in 82% yield, melting point 152°-153° (from ethyl acetate/hexane);

from ethyl 5-(3-cyanophenyl)-4-thiazolecarboxylate and t-butyl (2-aminoethyl)carbamate the t-butyl [2-[5-(3-cyanophenyl)-4-thiazolecarboxamido]ethyl]carbamate in 68% yield, melting point 127°-128° (from ethyl acetate/hexane);

from ethyl 5-(4-cyanophenyl)-4-thiazolecarboxylate and t-butyl (2-aminoethyl)carbamate the t-butyl [2-[5-(4-cyanophenyl)-4-thiazolecarboxamido]ethyl]carbamate in 60% yield, melting point 149°-149.5° (from ethyl acetate/hexane);

from ethyl 5-(2-thienyl)-4-thiazolecarboxylate and t-butyl (2-aminoethyl)carbamate the t-butyl [2-[5-(2-thienyl)-4-thiazolecarboxamido]ethyl]carbamate in 60% yield, melting point 100°-101° (from ethyl acetate/hexane);

from ethyl 5-(3-thienyl)-4-thiazolecarboxylate and t-butyl (2-aminoethyl)carbamate the t-butyl [2-[5-(3-thienyl)-4-thiazolecarboxamido]ethyl]carbamate in 43% yield, melting point 83° (from ether);

from ethyl 5-(5-bromo-2-thienyl)-4-thiazolecarboxylate and t-butyl (2-aminoethyl)carbamate the t-butyl [2-[5-(5-bromo-2-thienyl)-4-thiazolecarboxamido]ethyl]carbamate in 56% yield, melting point 144°-145° (from ethyl acetate/hexane); and from ethyl 5-(2-furyl)-4-thiazolecarboxylate and t-butyl (2-aminoethyl)carbamate the t-butyl [2-[5-(2-furyl)-4-thiazolecarboxamido]ethyl]carbamate in 56% yield, melting point 93°-94° (from ethyl acetate/hexane).

The following carbamates were prepared in an analogous manner to that described in Example 1(E):

From 5-(2,4-dichlorophenyl)-4-thiazolecarboxylic acid and t-butyl (2-aminoethyl)carbamate the t-butyl [2-[5-(2,4-dichlorophenyl)-4-thiazolecarboxamido]ethyl]carbamate in 92.2% yield, melting point 142° (from ethyl acetate/hexane);

from 5-(3,4-dichlorophenyl)-4-thiazolecarboxylic acid and t-butyl (2-aminoethyl)carbamate the t-butyl [2-[5-(3,4-dichlorophenyl)-4-thiazolecarboxamido]ethyl]carbamate in 82.1% yield, melting point 128° (from ethyl acetate/hexane);

from 5-(2,4-difluorophenyl)-4-thiazolecarboxylic acid and t-butyl (2-aminoethyl)carbamate the t-butyl [2-[5-(2,4-difluorophenyl)-4-thiazolecarboxamido]ethyl]carbamate in 73% yield, melting point 109°-110° (from ethyl acetate/hexane);

from 5-(2,3-dichlorophenyl)-4-thiazolecarboxylic acid and t-butyl (2-aminoethyl)carbamate the t-butyl [2-[5-(2,3-dichlorophenyl)-4-thiazolecarboxamido]ethyl]carbamate in 91% yield, melting point 144°-145° (from ethyl acetate/hexane);

from 5-(2,5-dichlorophenyl)-4-thiazolecarboxylic acid and t-butyl (2-aminoethyl)carbamate the t-butyl [2-[5-(2,5-dichlorophenyl)-4-thiazolecarboxamido]ethyl]carbamate in 90% yield, melting point 129°-130° (from ethyl acetate/hexane); and from 5-(3,4-difluorophenyl)-4-thiazolecarboxylic acid and t-butyl (2-aminoethyl)carbamate the t-butyl [2-[5-(3,4-difluorophenyl)-4-thiazolecarboxamido]ethyl]carbamate in 93% yield, melting point 115°-116° (from ethyl acetate/hexane).

The ethyl 4-thiazolecarboxylates used as starting materials are listed hereinafter. They were prepared in an analogous manner to that described in Example 1(C) by reacting the corresponding thioester with ethyl isocyanoacetate in the presence of potassium hydroxide.

From O-methyl 2-fluorothiobenzoate the ethyl 5-(2-fluorophenyl)-4-thiazolecarboxylate in 67.3% yield as a yellow oil;

from O-methyl 3-fluorothiobenzoate the ethyl 5-(3-fluorophenyl)-4-thiazolecarboxylate in 63.7% yield as a pale yellow oil:

from O-methyl 4-fluorothiobenzoate the ethyl 5-(4-fluorophenyl)-4-thiazolecarboxylate in 51% yield, melting point 65°-66° (from ethyl acetate/hexane); yellow oil:

from O-ethyl 2-chlorothiobenzoate the ethyl 5-(2-chlorophenyl)-4-thiazolecarboxylate in 30% yield as a yellow oil;

from O-ethyl 3-chlorothiobenzoate the ethyl 5-(3-chlorophenyl)-4-thiazolecarboxylate in 41% yield, melting point 73°-75° (from ether/petroleum ether);

from O-ethyl 4-chlorothiobenzoate the ethyl 5-(4-chlorophenyl)-4-thiazolecarboxylate in 57% yield, melting point 99°-100° (from ethyl acetate/hexane):

from O-methyl 3-bromothiobenzoate the ethyl 5-(3-bromophenyl)-4-thiazolecarboxylate in 42% yield, melting point 66°-67° (from ethyl acetate/hexane);

from O-methyl 3,5-dichlorothiobenzoate the ethyl 5-(3,5-dichlorophenyl)-4-thiazolecarboxylate in 54% yield as an oil;

from O-methyl 2-methylthiobenzoate the ethyl 5-(2-methylphenyl)-4-thiazolecarboxylate in 23% yield, melting point 72°-73° (from ethyl acetate/hexane):

from O-methyl 3-methylthiobenzoate the ethyl 5-(3-methylphenyl)-4-thiazolecarboxylate in 37% yield as a red-brown oil;

from O-methyl 4-methylthiobenzoate the ethyl 5-(4-methylphenyl)-4-thiazolecarboxylate in 52% yield, melting point 78°-79° (from ethyl acetate/hexane);

from O-methyl 2-methoxythiobenzoate the ethyl 5-(2-methoxyphenyl)-4-thiazolecarboxylate in 8.6% yield as a yellow oil;

from O-methyl 3-methoxythiobenzoate the ethyl 5-(3-methoxyphenyl)-4-thiazolecarboxylate in 25.6% yield as an oil;

from O-methyl 4-methoxythiobenzoate the ethyl 5-(4-methoxyphenyl)-4-thiazolecarboxylate in 48% yield, melting point 69°-70° (from ethyl acetate/hexane);

from O-methyl 3-($\alpha,\alpha,\alpha$-trifluoromethyl)thiobenzoate the ethyl 5-($\alpha,\alpha,\alpha$-trifluoro-3-methylphenyl)-4-thiazolecarboxylate in 51% yield as an oil;

from O-methyl 4-($\alpha,\alpha,\alpha$-trifluoromethyl)thiobenzoate the ethyl 5-($\alpha,\alpha,\alpha$-trifluoro-4-methylphenyl)-4-thiazolecarboxylate in 60% yield, melting point 124°-125° (from ethyl acetate/hexane);

from O-methyl 3-cyanothiobenzoate the ethyl 5-(3-cyanophenyl)-4-thiazolecarboxylate in 63% yield, melting point 149° (from ethyl acetate/hexane);

from O-methyl 4-cyanothiobenzoate the ethyl 5-(4-cyanophenyl)-4-thiazolecarboxylate in 37.6% yield, melting point 111°-112° (from ethyl acetate/hexane);

from O-methyl 2,4-dichlorothiobenzoate the ethyl 5-(2,4-dichlorophenyl)-4-thiazolecarboxylate in 66.6% yield, melting point 79°-80° (from ethyl acetate/hexane);

from O-methyl 3,4-dichlorothiobenzoate the ethyl 5-(3,4-dichlorophenyl)-4-thiazolecarboxylate in 80.6% yield, melting point 113° (from ethyl acetate/hexane):

from O-methyl 2,4-difluorothiobenzoate the ethyl 5-(2,4-difluorophenyl)-4-thiazolecarboxylate in 83% yield, melting point 73°-74° (from ethyl acetate/hexane);

from O-methyl 2-thiophenethiocarboxylate the ethyl 5-(2-thienyl)-4-thiazolecarboxylate in 63% yield, melting point 37°-38° (from ethyl acetate/hexane);

from O-methyl 3-thiophenethiocarboxylate the ethyl 5-(3-thienyl)-4-thiazolecarboxylate in 49% yield, melting point 65°-67° (from ethyl acetate/hexane);

from O-methyl 5-bromo-2-thiophenethiocarboxylate the ethyl 5-(5-bromo-2-thienyl)-4-thiazolecarboxylate in 48% yield, melting point 80°-86° (from ethyl acetate/hexane);

from O-methyl 2-furanthiocarboxylate the ethyl 5-(2-furyl)-4-thiazolecarboxylate in 70% yield, melting point 51°-52° (from ethyl acetate/hexane);

from O-methyl 2,3-dichlorothiobenzoate the ethyl 5-(2,3-dichlorophenyl)-4-thiazolecarboxylate in 83% yield, melting point 131° (from ethanol);

from O-methyl 2,5-dichlorothiobenzoate the ethyl 5-(2,5-dichlorophenyl)-4-thiazolecarboxylate in 56% yield, melting point 89°-90° (from ethyl acetate/hexane); and from O-methyl 3,4-difluorothiobenzoate the ethyl 5-(3,4-difluorophenyl)-4-thiazolecarboxylate in 78% yield, melting point 75° (from ethyl acetate/hexane).

The 4-thiazolecarboxylic acids used as starting materials were prepared from the corresponding ethyl 4-thiazolecarboxylates by hydrolysis in an analogous manner to that described in Example 1(D):

5-(2,4-Dichlorophenyl)-4-thiazolecarboxylic acid in 78% yield, melting point 185°-186° (from ethyl acetate/hexane);

5-(3,4-dichlorophenyl)-4-thiazolecarboxylic acid in 95% yield, melting point 202°-203° (from water):

5-(2,4-difluorophenyl)-4-thiazolecarboxylic acid in 95% yield, melting point 182°-183° (from water);

5-(2,3-dichlorophenyl)-4-thiazolecarboxylic acid in 97% yield, melting point 199°-201° (from water);

5-(2,5-dichlorophenyl)-4-thiazolecarboxylic acid in 95% yield, melting point 172°-173° (from water); and 5-(3,4-difluorophenyl)-4-thiazolecarboxylic acid in 55% yield, melting point 195°-196° (from water).

Finally, the thioesters used above as starting materials were obtained from the corresponding carboxylic acid esters by reaction with Lawesson reagent in an analogous manner to that described in Example 1(B):

O-Methyl 2-fluorothiobenzoate in 51% yield as a yellow oil;

O-methyl 3-fluorothiobenzoate in 53% yield as a yellow oil;

O-methyl 4-fluorothiobenzoate in 91% yield as a yellow oil;

O-ethyl 2-chlorothiobenzoate in 62% yield as a yellow oil;

O-ethyl 3-chlorothiobenzoate in 80% yield as a yellow oil;

O-ethyl 4-chlorothiobenzoate in 70% yield as an orange oil;

O-ethyl 3-bromothiobenzoate in 43% yield as a yellow oil;

O-methyl 3,5-dichlorothiobenzoate in 41% yield as a yellow oil;

O-methyl 2-methylthiobenzoate in 74% yield as a yellow oil;

O-methyl 3-methylthiobenzoate in 76% yield as a dark yellow oil;

O-methyl 4-methylthiobenzoate in 75% yield as a yellow oil;

O-methyl 2-methoxythiobenzoate in 50% yield as an orange oil;

O-methyl 3-methoxythiobenzoate in 72.5% yield as an orange oil;

O-methyl 4-methoxythiobenzoate in 52% yield as an orange oil;

O-methyl 3-($\alpha,\alpha,\alpha$-trifluoromethyl)thiobenzoate in 59% yield as a yellow oil;

O-methyl 4-($\alpha,\alpha,\alpha$-trifluoromethyl)thiobenzoate in 45% yield as a yellow oil;

O-methyl 3-cyanothiobenzoate in 43% yield as a yellow oil;

O-methyl 4-cyanothiobenzoate in 88% yield, melting point 53°-54° :

O-methyl 2,4-dichlorothiobenzoate in 20% yield as a yellow oil:

O-methyl 3,4-dichlorothiobenzoate in 50% yield as a yellow oil:

O-methyl 2,4-difluorothiobenzoate in 69.4% yield as a yellow oil;

O-methyl 2-thiophenethiocarboxylate in 93% yield as a yellow oil;

O-methyl 3-thiophenethiocarboxylate in 81% yield as a yellow oil;

O-methyl 5-bromo-2-thiophenethiocarboxylate in 79% yield as a yellow oil;

O-methyl 2-furanthiocarboxylate in 72.4% yield as an orange oil;

O-methyl 2,3-dichlorothiobenzoate in 36% yield- as a yellow oil;

O-methyl 2,5-dichlorothiobenzoate in 26% yield as a yellow oil; and

O-methyl 3,4-difluorothiobenzoate in 67% yield as a yellow oil.

EXAMPLE 3

In an analogous manner to that described in Example 1(A), from 19.4 g (42.8 mmol) of t-butyl [2-[5-[3-((benzyloxy)phenyl]-4-thiazolecarboxamido]ethyl]carbamate there were obtained 14.7 g (91%) of N-(2-aminoethyl)-5-[3-(benzyloxy)phenyl]-4-thiazolecarboxamide hydrochloride as beige crystals, melting point 230°-231° (from methanol).

The t-butyl [2-[5-[3-(benzyloxy)phenyl]-4-thiazolecarboxamido]ethyl]carbamate used as the starting material was prepared as follows:

In an analogous manner to that described in Example 1(B), 40 g (0.165 mol) of methyl 3-(benzyloxy)benzoate were heated at reflux for 8 hours with 33.4 g (0.0826 mol) of Lawesson reagent in xylene and thereafter chromatographed on silica gel, whereby there were obtained 21.7 g (51%) of O-methyl 3-(benzyloxy)thiobenzoate as a red-brown oil which gradually crystallized upon standing.

In an analogous manner to that described in Example 1(C), 21.7 g of O-methyl 3-(benzyloxy)thiobenzoate (44.13 mmol) were reacted with ethyl isocyanoacetate, whereby there were obtained 26.5 g (92.9%) of ethyl 5-[3-(benzyloxy)phenyl]-4-thiazolecarboxylate as an orange oil.

From 26.5 g (78.1 mmol) of ethyl 5-[3-(benzyloxy)phenyl]-4-thiazolecarboxylate there were obtained, by reaction with t-butyl (2-aminoethyl)carbamate, 19.4 g (54.8%) of t-butyl [2-[5-[3-(benzyloxy)phenyl]-4-thiazolecarboxamido]ethyl]carbamate as an oil which was used without further purification.

EXAMPLE 4

In an analogous manner to that described in Example 1(A). from 8.4 g (17.2 mmol) of t-butyl [2-[5-[3-[(3-chlorobenzyl)oxy]phenyl]-4-thiazolecarboxamido]ethyl]carbamate there were obtained 6.4 g of N-(2-aminoethyl)-5[3-[(3-chlorobenzyl)oxy]phenyl]-4-thiazolecarboxamide hydrochloride as white crystals, melting point 212°-213° (from methanol/ether, yield: 87.6%).

The t-butyl [2-[5-[3-[(3-chlorobenzyl)oxy]phenyl]-4thiazolecarboxamido]ethyl]carbamate used as the starting material was prepared as follows:

In an analogous manner to that described in Example 1(B). 36.5 g (131.9 mmol) of methyl 3-[(3-chlorobenzyl)oxy]benzoate were heated at reflux for 16 hours with 26.7 g (66 mmol) of Lawesson reagent in xylene and thereafter chromatographed on silica gel. Elution with hexane/toluene (2%, 5% and 10%) yielded 28.2 g (73%) of O-methyl 3-[(3-chlorobenzyl)oxy]thiobenzoate as an orange, crystallizing oil.

In an analogous manner to that described in Example 1(C). 28.2 g (96.3 mmol) of O-methyl 3-[(3-chlorobenzyl)oxy]thiobenzoate were reacted with ethyl isocyanoacetate and subsequently chromatographed on silica gel. Elution with 9:1, 8:2 and 1:1 mixtures of methylene chloride and ethyl acetate as well as ethyl acetate alone yielded 28 g (77.8%) of ethyl 5-[3-[(3-chlorobenzyl)oxy]phenyl]-4-thiazolecarboxylate as an orange oil.

From 10.0 g (26.75 mmol) of ethyl 5-[3-[(3-chlorobenzyl)oxy]phenyl]-4-thiazolecarboxylate there were obtained by reaction with t-butyl (2-aminoethyl)carbamate 10.5 g of crystals which were recrystallized from ethyl acetate/hexane. In this manner there were obtained 8.4 g (64.4%) of t-butyl [2-[5-[3-[(3-chlorobenzyl)oxy]phenyl]-4-thiazolecarboxamido]ethyl]carbamate as white crystals, melting point 116°–117°.

EXAMPLE 5

In an analogous manner to that described in Example 1(A). from 2.9 g (6.06 mmol) of t-butyl [2-(5-(3-[(3cyanobenzyl)oxy]phenyl]-4-thiazolecarboxamido)ethyl]carbamate there were obtained 2.1 g (83.5%) of N-(2-aminoethyl)-5-(3-[(3-cyanobenzyl)oxy]phenyl)-4-thiazolecarboxamide hydrochloride as white crystals, melting point 211°–215° (from methanol/ether).

The t-butyl [2-(5-(3-[(3-cyanobenzyl)oxy]phenyl]-4-thiazolecarboxamido)ethyl]carbamate used as the starting material was prepared as follows:

In an analogous manner to that described in Example 1(B). 8.9 g (33.3 mmol) of methyl 3-[(3-cyanobenzyl)oxy]benzoate were heated to reflux for 17 hours with 13.5 g (33.4 mmol) of Lawesson reagent in xylene and thereafter chromatographed on silica gel. Elution with an 8:2 and 7:3 mixture of hexane and methylene chloride yielded 7.6 g (65.8%) of O-methyl 3-[(3-cyanobenzyl)oxy]thiobenzoate as a yellow oil which gradually crystallized upon standing.

7.6 g (26.82 mmol) of O-methyl 3-[(3-cyanobenzyl)oxy]thiobenzoate were dissolved in 50 ml of ethanol together with 3.6 g (32.1 mmol) of ethyl isocyanoacetate and added dropwise at room temperature to a solution of 0.4 g of potassium hydroxide in 30 ml of ethanol. After completion of the addition the reaction mixture was heated to reflux while stirring for a further 20 hours and then evaporated. The residue was partitioned between ether and water, the aqueous phase was extracted a further time twice with ether and the combined organic phases were washed with water and saturated sodium chloride solution, dried over magnesium sulfate, filtered and evaporated. The residue was chromatographed on 150 g of silica gel with methylene chloride and methylene chloride which contains 5% and, respectively, 10% of ethyl acetate as the eluting agent. The pure fractions were combined and evaporated, whereby there were obtained 4.5 g of an oil which was crystallized from ethyl acetate/hexane. In this manner there were obtained 3.5 g (36%) of ethyl 5-[3-[(3-cyanobenzyl)oxy]phenyl]-4-thiazolecarboxylate as beige crystals, melting point 85°.

From 3.5 g (9.6 mmol) of ethyl 5-[3-[(3-cyanobenzyl)oxy]phenyl]-4-thiazolecarboxylate there were obtained by reaction with t-butyl (2-aminoethyl)carbamate in an analogous manner to that described in Example 1(E1) and subsequent chromatography on silica gel with a 9:1 and 8:2 mixture of methylene chloride and ethyl acetate as the eluting agent 3.4 g of an oil which crystallized from ethyl acetate/hexane. In this manner there were obtained 3.0 g (65.3%) of t-butyl [2-(5-(3-[(3-cyanobenzyl)oxy]phenyl]4-thiazolecarboxamido)ethyl]carbamate as white crystals, melting point 115°.

EXAMPLE 6

2.0 g (5.5 mmol) of t-butyl [2-(2-amino-5-phenyl-4thiazolecarboxamido)ethyl]carbamate were dissolved in 15 ml of methylene chloride and heated to reflux for 3 hours with 2.1 ml (27.6 mmol) of trifluoroacetic acid. Thereafter, the reaction mixture was evaporated under reduced pressure and the residue was dissolved in methanol, treated with ~2 M methanolic hydrochloric acid and evaporated. Recrystallization of the residue from methanol/ether with the addition of a small amount of hexane yielded 1.65 g (90%) of 2-amino-N-(2-aminoethyl)-5-phenyl-4-thiazolecarboxamide dihydrochloride as white crystals, melting point 203°–205°.

The following two compounds were prepared in an analogous manner to that described above:

From 0.9 g (2.27 mmol) of t-butyl [2-(2-amino-5-(4-chlorophenyl)-4-thiazolecarboxamido)ethyl]carbamate 0.8 g (95%) of 2-amino-N-(2-aminoethyl)-5-(4-chlorophenyl)-4thiazolecarboxamide dihydrochloride as white crystals. melting point 228°–230°; and from 2.1 g (5.52 mmol) of t-butyl [2-(2-amino-5-(3-fluorophenyl)-4-thiazolecarboxamido)ethyl]carbamate 0.7 g (36%) of 2-amino-N-(2-aminoethyl)-5-(3-fluorophenyl)-4-thiazolecarboxamide hydrochloride as white crystals, melting point 296°–297°.

The t-butyl [2-(2-amino-5-phenyl-4-thiazolecarboxamido)ethyl]carbamate used as the starting material was prepared as follows:

5.0 g (21.3 mmol) of methyl 2-amino-5-phenyl-4-thiazolecarboxylate (which was prepared as described in J. Chem. Soc. Perk. Trans. I (1982) 159–164) and 6.84 g (42.7 mmol) of t-butyl (2-aminoethyl)carbamate were heated under reduced pressure for 2 hours at a bath temperature of 140°, whereby the methanol formed was distilled off continuously. After cooling the residue was dissolved in 50 ml of methylene chloride and chromatographed on 200 g of silica gel with a 9:1 mixture of methylene chloride and methanol as the eluting agent. The fractions which were pure according to the thin-layer chromatogram were combined and evaporated under reduced pressure, whereby there were obtained 4.5 g of a red, crystallizing oil. Crystallization from methanol and an ether/hexane mixture yielded 3.48 g (45%) of t-butyl [2-(2-amino-5-phenyl-4thiazolecarboxamido)ethyl]carbamate as beige crystals which were used without further purification.

The following two carbamates were prepared in an analogous manner to that described above:

From 4.0 g (14.89 mmol) of methyl 2-amino-5-(4-chlorophenyl)-4-thiazolecarboxylate 1.2 g (20%) of t-butyl [2-(2-amino-5-(4-chlorophenyl)-4-thiazolecarboxamido)ethyl]carbamate as almost white crystals, melting point 156°–157°; and from 5.0 g (19.82 mmol) of methyl 2-amino-5-(3-fluorophenyl)-4-thiazolecarboxylate 2.1 g (27.5%) of t-butyl [2 (2-amino-5-(3-fluorophenyl)-4-thiazolecarboxamido)ethyl]carbamate as white crystals, melting point 178°-179°

The two methyl esters used as starting materials were prepared according to the method described in J. Chem. Soc. Perk. Trans. 1 (1982) 159-164:

Methyl 2-amino-5-(4-chlorophenyl)-4-thiazolecarboxylate in 95% yield, melting point 242°-244° (from water); and methyl 2-amino-5-(3-fluorophenyl)-4-thiazolecarboxylate in 86.9% yield, melting point 224°-226°.

EXAMPLE 7

In an analogous manner to that described in Example 6, from 1.55 g (4.1 mmol) of t-butyl [2-(2-chloro-5-phenyl-4-thiazolecarboxamido)ethyl]carbamate there were obtained 1.23 g (94%) of N-(2-aminoethyl)-2-chloro-5-phenyl-4-thiazolecarboxamide hydrochloride as white crystals. melting point 186°-187°.

The t-butyl [2-(2-chloro-5-phenyl-4-thiazolecarboxamido)ethyl]carbamate used as the starting material was prepared as follows:

14.04 g (60 mmol) of methyl 2-amino-5-phenyl-4-thiazolecarboxylate were reacted as described in J. Chem. Soc. Perk. Trans. I (1982), pp 159-164; there were obtained about 15 g of a yellow oil. Chromatography on silica gel with methylene chloride as the eluting agent and crystallization of the crude product obtained from ether/hexane yielded 10.6 q (70%) of methyl 2-chloro-5-phenyl-4-thiazolecarboxylate as crystals, melting point 68°-69°.

5.4 g (21.3 mmol) of methyl 2-chloro-5-phenyl-4-thiazolecarboxylate and 3.6 g (22.3 mmol) of t-butyl (2-aminoethyl)carbamate were stirred under reduced pressure for 22 hours at a bath temperature of 110°, whereby the methanol formed was distilled off continuously. The reaction mixture was cooled, dissolved in methylene chloride and chromatographed on 150 g of silica gel with methylene chloride and a 4:1 mixture of methylene chloride and ethyl acetate as the eluting agent. The fractions which were pure according to the thin-layer chromatogram were combined and evaporated. Crystallization of the residue from ethyl acetate/hexane yields 1.83 g (27.5%) of t-butyl [2-(2-chloro-5-phenyl-4-thiazolecarboxamido)ethyl]carbamate as white crystals, melting point 114°-116°.

EXAMPLE 8

In an analogous manner to that described in Example 6. from 1.2 g (3.0 mmol) of t-butyl [2-(2-chloro-5-(3-fluorophenyl)-4-thiazolecarboxamido)ethyl]carbamate there was obtained 0.75 g (76%) of N-(2-aminoethyl)-2-chloro-5-(3-fluorophenyl)-4-thiazolecarboxamide hydrochloride as white crystals, melting point 206°-207°.

The t-butyl [2-(2-chloro-5-(3-fluorophenyl)-4thiazolecarboxamido)ethyl]carbamate used as the starting material was prepared as follows:

In an analogous manner to that described in Example 7, from 5.0 g (19.82 mmol) of methyl 2-amino-5-(3-fluorophenyl)-4-thiazolecarboxylate there were obtained 2.0 g (37.1%) of methyl 2-chloro-5-(3-fluorophenyl)-4-thiazolecarboxylate as white crystals, melting point 99°-100° (from ethyl acetate/hexane).

In an analogous manner to that described in Example 7, from 2.6 g (9.57 mmol) of methyl 2-chloro-5-(3-fluorophenyl)-4-thiazolecarboxylate there were obtained 1.2 g (32%) of t-butyl [2-(2-chloro-5-(3-fluorophenyl)-4-thiazolecarboxamido)ethyl]carbamate as white crystals which were used directly.

EXAMPLE 9

0.5 g (1.2 mmol) of t-butyl [2-(2-bromo-5-phenyl-4-thiazolecarboxamido)ethyl]carbamate, 2 ml of trifluoroacetic acid and 10 ml of methylene chloride were heated to reflux for 2 hours and then evaporated. The residue was dissolved in methanol and treated with 1 ml of hydrobromic acid in glacial acetic acid (- 30%). Renewed evaporation and recrystallization of the residue from methanol/ether yields 0.45 g (94.2%) of N-(2-aminoethyl)-2-bromo-5-phenyl-4-thiazolecarboxamide hydrobromide as beige crystals, melting point 214°-215° (dec.).

The t-butyl [2-(2-bromo-5-phenyl-4-thiazolecarboxamido)ethyl]carbamate used as the starting material was prepared as follows:

From 7.02 g (30 mmol) of methyl 2-amino-5-phenyl-4thiazolecarboxylate, 15.48 g (62 mmol) of copper sulfate. 13.73 g (133 mmol) of sodium bromide. 5.1 g (73.9 mmol) of sodium nitrite and 300 g of conc. sulfuric acid 1n 225 ml of water there were obtained in an analogous manner to that described in Example 7 7.0 g (78%) of methyl 2-bromo-5-phenyl-4-thiazolecarboxylate as crystals which melted at 86°-87° after recrystallization from ether/hexane.

2.0 g (6.7 mmol) of methyl 2-bromo-5-phenyl-4thiazolecarboxylate and 1.61 g (10.1 mmol) of t-butyl (2-aminoethyl)carbamate were stirred under reduced pressure for 2.5 hours at 110° bath temperature, whereby the methanol formed was distilled off continuously. After chromatography on 100 g of silica gel with methylene chloride and a 4:1 mixture of methylene chloride and ethyl acetate there was obtained 0.58 g (26%) of t-butyl [2-(2-bromo-5-phenyl-4-thiazolecarboxamido)ethyl]carbamate as a pale yellow, crystallizing oil which was used directly.

EXAMPLE 10

3.6 g (19.1 mmol) of 5-phenyl-4-oxazolecarboxylic acid were added portionwise to a suspension of 3.1 g (19.1 mmol) of 1,1'-carbonyldiimidazole in 20 ml of dry tetrahydro-furan, whereby a brown solution formed with o the evolution of gas. After a reaction period of 15 minutes at 20° 3.05 g (19.0 mmol) of t-butyl (2-aminoethyl)carbamate in 10 ml of dry tetrahydrofuran were added dropwise (slight warming) and the reaction mixture was stirred for a further 30 minutes. Thereafter, the reaction mixture was evaporated under reduced pressure and the residue was partitioned between methylene chloride and 0.1 N hydrochloric acid. After washing neutral with saturated sodium chloride solution the organic phase was dried over magnesium sulfate and evaporated, whereby there were obtained 5.8 g (92%) of t-butyl [2-(5-phenyl-4-oxazole- carboxamido)ethyl]carbamate which were stirred at 20° for 20 minutes in 20 ml of trifluoroacetic acid. Thereafter, the reaction mixture was evaporated under reduced pressure. The residue was dissolved in 5 ml of methanol and treated with 10 ml of 5.5 N hydrogen chloride in methanol. Filtration of the separated crystals yielded 2.4 g (51%) of N-(2-aminoethyl)-5-phenyl-4-oxazole- carboxamide hydrochloride as white crystals, melting point 257° (dec.). The 5-phenyl-4-oxazolecarboxylic acid used as the starting material was prepared as follows: Analogously to the method described in Tetrahedron Letters, 23, 235-236 (1982), from ethyl isocyanoacetate, benzoic acid, phosphoric acid diphenyl ester azide and potassium carbonate in dimethylformamide/water there was prepared ethyl 5-phenyl-4-oxazolecarboxylate which was then converted into the desired acid likewise according to known methods by hydrolysis with 2N sodium hydroxide solution at 50° during 15 minutes.

EXAMPLE 11

The following compounds were prepared in an analogous manner to that described in Example 10:

From t-butyl [2-[5-(2-chlorophenyl)-4-oxazolecarboxamido]ethyl]carbamate the N-(2-aminoethyl)-5-(2-chlorophenyl)-4-oxazolecarboxamide hydrochloride in 66.4% yield, melting point 247°-248° (from methanol/diethyl ether);

from t-butyl [2-[5-(3-chlorophenyl)-4-oxazolecarboxamido]ethyl]carbamate the N-(2-aminoethyl)-5-(3-chlorophenyl)-4-oxazolecarboxamide hydrochloride in 86.5% yield, melting point 229°-231° (from methanol/diethyl ether);

from t-butyl [2-[5-(4-chlorophenyl)-4-oxazolecarboxamido]ethyl]carbamate the N-(2-aminoethyl)-5-(4-chlorophenyl)-4-oxazolecarboxamide hydrochloride in 73.4% yield, melting point 274°-275° (from methanol/diethyl ether);

from t-butyl [2-[5-(2-fluorophenyl)-4-oxazolecarboxamido]the N-(2-aminoethyl)-5-(2-fluorophenyl)-4-oxazolecarboxamide hydrochloride in 65.4% yield, melting point 271°-272° (from from t-butyl [2-[5-(3-fluorophenyl)-4-oxazolecarboxamido]ethyl]carbamate the N-(2-aminoethyl)-5-(3-fluorophenyl)-4-oxazolecarboxamide hydrochloride in 95% yield, melting point 258°-260° (from methanol/diethyl ether);

from t-butyl [2-[5-(4-fluorophenyl)-4-oxazolecarboxamido]ethyl]carbamate the N-(2-aminoethyl)-5-(4-fluorophenyl)-4-oxazolecarboxamide hydrochloride in 84% yield, melting point 287° (from methanol/diethyl ether);

from t-butyl [2-[5-(4-bromophenyl)-4-oxazolecarboxamido]ethyl]carbamate the N-(2-aminoethyl)-5-(4-bromophenyl)-4-oxazolecarboxamide hydrochloride in 89% yield, melting point 254°-256° (from methanol/diethyl ether);

from t-butyl [2-[5-(3,4-dichlorophenyl)-4-oxazolecarboxamido]ethyl]carbamate the N-(2-aminoethyl)-5-(3,4-dichlorophenyl)-4-oxazolecarboxamide hydrochloride in 98% yield, melting point 275°-276° (from methanol);

from t-butyl [2-[5-(2-furyl)-4-oxazolecarboxamido]ethyl]carbamate the N-(2-aminoethyl)-5-(2-furyl)-4-oxazolecarboxamide hydrochloride in 95% yield, melting point 238°-239° (from methanol/diethyl ether]-carbamate from t-butyl [2-[5-(2-thienyl)-4-oxazolecarboxamid]ethyl]carbamate the N-(2-aminoethyl)-5-(2-thienyl)4-oxazolecarboxamide hydrochloride in 71% yield, melting point 263°-264° (from methanol/diethyl ether);

from t-butyl butyl [2-[5-(5-bromo-2-furyl)-4-oxazolecarboxamido]ethyl]carbamate the N-(2-aminoethyl)-5-(5-bromo-2-furyl)-4-oxazolecarboxamide hydrochloride in 91% yield, melting point 231°-233° (from methanol/diethyl ether);

from t-butyl [2-[5-(2,4-difluorophenyl)-4-oxazolecarboxamido]ethyl]carbamate the N-(2-aminoethyl)-5-(2.4-difluorophenyl)-4-oxazolecarboxamide hydrochloride in 91% yield, melting point >290° (from methanol); and from t-butyl [2-[5-(2,6-difluorophenyl)-4-oxazolecarboxamido]ethyl]carbamate the N-(2-aminoethyl)-5-(2,6-difluorophenyl)-4-oxazolecarboxamide hydrochloride in 80% yield, melting point 266°-267° (from methanol).

The carbamates used as starting materials were prepared in an analogous manner to that described in Example 1(E1):

From ethyl 5-(2-chlorophenyl)-4-oxazolecarboxylate and t-butyl (2-aminoethyl)carbamate the t-butyl [2-[5-(2-chlorophenyl)-4-oxazolecarboxamido]ethyl]carbamate in 38% yield (was processed without further purification);

from ethyl 5-(3-chlorophenyl)-4-oxazolecarboxylate and t-butyl (2-aminoethyl)carbamate the t-butyl [2-[5-(3-chlorophenyl)-4-oxazolecarboxamido]ethyl]carbamate in 38% yield, melting point 140°-141° (from ethyl acetate/hexane);

from ethyl 5-(4-chlorophenyl)-4-oxazolecarboxylate and t-butyl (2-aminoethyl)carbamate the t-butyl [2-[5-(4-chlorophenyl)-4-oxazolecarboxamido]ethyl]carbamate in 49% yield, melting point 164° (from ethyl acetate/hexane);

from ethyl 5-(2-fluorophenyl)-4-oxazolecarboxylate and t-butyl (2-aminoethyl)carbamate the t-butyl [2-[5-(2-fluorophenyl)-4-oxazolecarboxamido]ethyl]carbamate in 58% yield, melting point 130°-133° (from ethyl acetate/hexane);

from ethyl 5-(3-fluorophenyl)-4-oxazolecarboxylate and t-butyl (2-aminoethyl)carbamate the t-butyl [2-[5-(3-fluorophenyl)-4-oxazolecarboxamido]ethyl]carbamate in 69% yield, melting point 135°-136° (from ethyl acetate/hexane);

from ethyl 5-(4-fluorophenyl)-4-oxazolecarboxylate and t-butyl (2-aminoethyl)carbamate the t-butyl [2-[5-(4-fluorophenyl)-4-oxazolecarboxamido]ethyl]carbamate in 24% yield, melting point 146°-148° (from ethyl acetate/hexane);

from ethyl 5-(4-bromophenyl)-4-oxazolecarboxylate and t-butyl (2-aminoethyl)carbamate the t-butyl [2-[5-(4-bromophenyl)-4-oxazolecarboxamido]ethyl]carbamate in 32% yield, melting point 170°-171° (from ethyl acetate/hexane);

from ethyl 5-(3,4-dichlorophenyl)-4-oxazolecarboxylate and t-butyl (2-aminoethyl)carbamate the t-butyl [2-[5-(3,4-dichlorophenyl)-4-oxazolecarboxamido]ethyl]carbamate in 72% yield, melting point 126°-128° (from ethyl acetate/hexane);

from ethyl 5-(2-furyl)-4-oxazolecarboxylate and t-butyl (2-aminoethyl)carbamate the t-butyl [2-[5-(2-furyl)-4-oxazolecarboxamido]ethyl]carbamate in 32% yield, melting point 86°-87° (from ethyl acetate/hexane); and from ethyl 5-(2-thienyl)-4-oxazolecarboxylate and t-butyl (2-aminoethyl)carbamate the t-butyl [2-[5-(2-thienyl)-4-oxazolecarboxamido]ethyl]carbamate in 12% yield, melting point 109°-110° (from ethyl acetate/hexane).

The following carbamates were prepared in an analogous manner to that described in Example 1(E):

From 5-(5-bromo-2-furyl)-4-oxazolecarboxylic acid and t-butyl (2-aminoethyl)carbamate the t-butyl [2-[5-(5-bromo-2-furyl)-4-oxazolecarboxamido]ethyl]carbamate in 97% yield, melting point 120°-121° (from ethyl acetate/ hexane);

from 5-(2,4-difluorophenyl)-4-oxazolecarboxylic acid and t-butyl (2-aminoethyl)carbamate the t-butyl [2-[5(2.4-difluorophenyl)-4-oxazolecarboxamido]ethyl]- carbamate in 92% yield, melting point 133° (from ethyl acetate/ hexane); and

- from 5-(2,6-difluorophenyl)-4-oxazolecarboxylic acid and t-butyl (2-aminoethyl)carbamate the t-butyl [2-[5-2,6-difluorophenyl)-4-oxazolecarboxamido]ethyl]carbamate in 61% yield, melting point 166°-167° (from ethyl acetate/hexane).

The ethyl carboxylates used as starting materials were prepared analogously to the method described in Tetrahedron Letters, 23, 235-236 (1982) from ethyl isocyanoacetate, the corresponding substituted benzoic acids or furancarboxylic acids or thiophenecarboxylic acids, phosphoric acid diphenyl ester azide and potassium carbonate:

From 2-chlorobenzoic acid and ethyl isocyanoacetate the ethyl 5-(2-chlorophenyl)-4-oxazolecarboxylate in 58% yield as a yellow oil (was processed without further purification);

from 3-chlorobenzoic acid and ethyl isocyanoacetate the ethyl 5-(3-chlorophenyl)-4-oxazolecarboxylate in 57% yield, melting point 57°-58° (from ethyl acetate/hexane);

from 4-chlorobenzoic acid and ethyl isocyanoacetate the ethyl 5-(4-chlorophenyl)-4-oxazolecarboxylate in 76% yield, melting point 103°-105° (from ethyl acetate/hexane);

from 2-fluorobenzoic acid and ethyl isocyanoacetate the ethyl 5-(2-fluorophenyl)-4-oxazolecarboxylate in 41% yield, melting point 62°-63° (from ethyl acetate/hexane);

from 3-fluorobenzoic acid and ethyl isocyanoacetate the ethyl 5-(3-fluorophenyl)-4-oxazolecarboxylate in 84% yield, melting point 48°-49° (from ethyl acetate/hexane);

from 4-fluorobenzoic acid and ethyl isocyanoacetate the ethyl 5-(4-fluorophenyl)-4-oxazolecarboxylate in 51% yield, melting point 53°-54° (from ethyl acetate/hexane);

from 4-bromobenzoic acid and ethyl isocyanoacetate the ethyl 5-(4-bromophenyl)-4-oxazolecarboxylate in 62% yield, melting point 118°-119° (from ethyl acetate/hexane);

from 3.4-dichlorobenzoic acid and ethyl isocyanoacetate the ethyl 5-(3,4-dichlorophenyl)-4-oxazolecarboxylate in 42% yield, melting point 102°-103° (from ethyl acetate/ hexane);

from 2-furancarboxylic acid and ethyl isocyanoacetate the ethyl 5-(2-furyl)-4-oxazolecarboxylate in 52% yield, melting point 97°-98° (from ethyl acetate/hexane);

from 2-thiophenecarboxylic acid and ethyl isocyanoacetate the ethyl 5-(2-thienyl)-4-oxazolecarboxylate in 26% yield, melting point 41°-42° (from ethyl acetate/hexane);

from 5-bromo-2-furancarboxylic acid and ethyl isocyanoacetate the ethyl 5-(5-bromo-2-furyl)-4-oxazolecarboxylate in 32% yield, melting point 93° (from ethyl acetate/hexane);

from 2,4-difluorobenzoic acid and ethyl isocyanoacetate the ethyl 5-(2,4-difluorophenyl)-4-oxazolecarboxylate in 13% yield, melting point 76°-77° (from ethyl acetate/hexane); and from 2.6-difluorobenzoic acid and ethyl isocyanoacetate the ethyl 5-(2.6-difluorophenyl)-4-oxazolecarboxylate in 13% yield as a yellow oil which crystallized upon standing.

The following carboxylic acids were prepared in an analogous manner to that described in Example 1(D):

From ethyl 5-(5-bromo-2-furyl)-4-oxazolecarboxylate the 5-(5-bromo-2-furyl)carboxylic acid in 66% yield, melting point 226°-228° (from ethyl acetate/hexane);

from ethyl 5-(2,4-difluorophenyl)-4-oxazolecarboxylate the 5-(2,4-difluorophenyl)-4-oxazolecarboxylic acid in 72% yield, melting point 180°-182° (from water); and from ethyl 5-(2,6-difluorophenyl)-4-oxazolecarboxylate the 5-(2.6-difluorophenyl)-4-oxazolecarboxylic acid in 64% yield (was used without further purification).

EXAMPLE 12

1.46 g (4.2 mmol) of t-butyl [2-(2-amino-5-phenyl-4-oxazolecarboxamido)ethyl]carbamate were dissolved in 50 ml of methylene chloride and treated with 5 ml of trifluoroacetic acid. The reaction mixture was heated to reflux while stirring for 2.5 hours and thereafter evaporated under reduced pressure. The residue was dissolved in methanol, treated with 5 ml of 2M methanolic hydrochloric acid and evaporated. Recrystallization of the residue from methanol/diethyl ether yielded 1.3 g (94%) of 2-amino-N-(2-aminoethyl)-5-phenyl-4-oxazolecarboxamide dihydrochloride as white crystals, melting point 260°.

The t-butyl [2-(2-amino-5-phenyl-4-oxazolecarboxamido)ethyl]carbamate used as the starting material was prepared as follows:

A solution of 3 q (0.13 gram atom) of sodium in 50 ml of methanol were added dropwise at 0°-5° within 20 minutes to a solution, cooled to 0°. of 16.1 g (152 mmol) of benzaldehyde and 20.0 g (140 mmol) of methyl dichloroacetate in 50 ml of ether. Thereafter, the reaction mixture was stirred at 0°-5° for a further 1.5 hours, then diluted with 100 ml of ethyl acetate and extracted with saturated sodium chloride solution. The organic phase was dried over magnesium sulfate and evaporated. The residue was dissolved in 50 ml of methanol and heated to reflux for 14 hours with 6.72 g (112 mmol) of urea. The reaction mixture was evaporated under reduced pressure, partitioned between methylene chloride and water, adjusted to pH 9 with conc. sodium hydroxide solution and extracted. The alkaline, aqueous phases were further extracted with methylene chloride. The organic phases were combined and washed twice with saturated sodium chloride solution, dried and evaporated. The residue was purified by medium pressure chromatography on 1 kg of silica gel. Elution with methylene chloride as well as methylene chloride/methanol 9:1 yielded 8.4 g of an oil which crystallized from a mixture of methylene chloride, ether and hexane. In this manner there were obtained 4.7 g (35%) of methyl 2-amino-5-phenyl-4-oxazolecarboxylate as light yellowish crystals which were processed without further purification.

2.0 g (9.2 mmol) of methyl 2-amino-5-phenyl-4-oxazolecarboxylate were stirred with 4.4 g (27,5 mmol) of t-butyl (2-aminoethyl)carbamate under reduced pressure for 6 hours at 120°. The reaction mixture was then chromatographed on 200 g of silica gel using ethyl acetate with the addition of 5% methanol as the eluting agent. The fractions which were pure according to the thin-layer chromatogram were crystallized from methylene chloride/ether/hexane and yield 1.46 g (62%) of t-butyl [2-(2-amino-5-phenyl-4-oxazolecarboxamido)ethyl]carbamate as white crystals which were processed without further purification.

EXAMPLE 13

1.5 g (4.33 mmol) of t-butyl [2-(5-amino-4-phenyl-3-isoxazolecarboxamido)ethyl]carbamate in 5 ml of methylene chloride were stirred at room temperature for 16 hours with 1.7 ml of trifluoroacetic acid. Thereafter, the reaction mixture was evaporated under reduced pressure: the residue was dissolved in ethanol, whereupon the solution was treated with 2 ml of ethanolic hydrochloric acid (17.5% w/v) and again evaporated. Recrystallization of the residue from methanol/ether yielded 0.9 g (73.5%) of 5-amino-N-(2-aminoethyl)-4-phenyl-3-isoxazolecarboxamide hydrochloride as white crystals, melting point 187°–189°.

The t-butyl [2-(5-amino-4-phenyl-3-isoxazolecarboxamido)ethyl]carbamate used as the starting material was prepared as follows:

Reaction of benzyl cyanide, sodium ethylate and diethyl oxalate according to the method described in Org. Synth. Coll. Vol. II (1943) 287 and Chem. Ber. 107 (1974) 2794–2795 in alcohol, acidification with conc. (37%) hydrochloric acid to pH 2 and subsequent recrystallization of the separated precipitate from ethanol yielded ethyl phenylcyanopyruvate in 90% yield as yellow crystals, melting point 127°–128°.

5.0 g (23 mmol) of ethyl phenylcyanopyruvate were reacted according to the method described in Chem. Ber. 107 (1974) 2794–2795 and Ber. Deutsch. Chem. Ges. 33 (1900) 2592–2595. Whereby there was obtained in 69.7% yield ethyl 5-amino-4-phenyl-3-isoxazolecarboxylate as beige crystals which melted at 119°–121° after recrystallization from ethyl acetate/hexane.

2.9 g (12.5 mmol) of ethyl 5-amino-4-phenyl-3-isoxazolecarboxylate were heated to 110° for 2 hours under reduced pressure with 5.0 g (31.2 mmol) of t-butyl (2-aminoethyl)carbamate, whereby the ethanol formed was distilled off continuously. The cooled reaction mixture was dissolved in methylene chloride and chromatographed on 100 g of silica gel. Elution with methylene chloride which contains 5%. 10% and, respectively, 20% of ethyl acetate, combining of the pure fractions and evaporation yielded 1.9 g of crystals. Recrystallization from ethyl acetate/hexane yielded 1.5 g (34.7%) of t-butyl [2-(5-amino-4-phenyl-3-isoxazolecarboxamido)ethyl]carbamate as white crystals, melting point 144°.

EXAMPLE 14

5.0 % (15.1 mmol) of t-butyl [2-(4-phenyl-3-isoxazolecarboxamido)ethyl]carbamate were stirred at room temperature for 16 hours with trifluoroacetic acid analogously to Example 13. After concentration there was obtained a residue which was converted into the hydrochloride. Recrystallization of the crude product from methanol/ether yielded 3.B g (94.1%) of N-(2-aminoethyl)4-phenyl-3-isoxazolecarboxamide hydrochloride as white crystals, melting point 211°–212°.

The t-butyl [2-(4-phenyl-3-isoxazolecarboxamido)ethyl]carbamate used as the starting material was prepared as follows:

In an analogous manner to that described in J. Org. Chem. 50 (13) 1985, 2372–2375, 7.6 g (32.72 mmol) of ethyl 5-amino-4-phenyl-3-isoxazolecarboxylate in 160 ml of glacial acetic acid, 50 ml of water and 80 ml of tetrahydrofuran were treated portionwise at 15°–20° while stirring within 1 hour with a total of 22.6 g of sodium nitrite. The reaction mixture was thereafter poured into 1 liter of water and extracted 3 times with 400 ml of methylene chloride each time. The organic phases were combined and first washed twice with 1 liter of saturated sodium bicarbonate solution each time and then once with 1 liter of water, dried, filtered and concentrated in a vacuum, whereby after chromatography on silica gel and elution with methylene chloride there were obtained 3.9 g (55%) of ethyl 4-phenyl-3-isoxazolecarboxylate as a yellow oil which was used without further purification.

3.9 g (17.95 mmol) of ethyl 4-phenyl-3-isoxazolecarboxylate and 5.8 g (36.2 mmol) of t-butyl (2-aminoethyl)carbamate were heated together to 110° for 2 hours under reduced pressure. Chromatography on silica gel and elution with methylene chloride which contained 5% and, respectively, 10% of ethyl acetate yielded an oil which crystallized from ethyl acetate/hexane. In this manner there were obtained 5.0 g (84%) of t-butyl [2-(4-phenyl-3-isoxazolecarboxamido)ethyl]carbamate as white crystals. melting point 170°–171°.

Example 15

The following compounds were prepared in an analogous manner to that described in Examples 13 and 14:

From t-butyl [2-[4-(2-chlorophenyl)-3-isoxazolecarboxamido]ethyl]carbamate the N-(2-aminoethyl)-4-(2-32.8% yield, melting point 255°–256° (from methanol/diethyl ether):

from t-butyl [2-[4-(3-chlorophenyl)-3-isoxazolecarboxamido]ethyl]carbamate the N-(2-aminoethyl)-4-(3-chlorophenyl)-3-isoxazolecarboxamide hydrochloride in 93% yield, melting point 181°–183° (from methanol/diethyl ether);

from t-butyl [2-[4-(4-chlorophenyl)-3-isoxazolecarboxamido]ethyl]carbamate the N-(2-aminoethyl)-4-(4-chlorophenyl)-3-isoxazolecarboxamide hydrochloride in 72% yield, melting point 254°–256° (from methanol/diethyl ether);

from t-butyl [2-[4-(3-fluorophenyl)-3-isoxazolecarboxamido]ethyl]carbamate the N-(2-aminoethyl) 4-(3-fluorophenyl)-3-isoxazolecarboxamide hydrochloride in 91.7% yield, melting point 183°–186° (from methanol/diethyl ether); and from t-butyl [2-[4-(4-fluorophenyl)-3-isoxazolecarboxamido]ethyl]carbamate the N-(2-aminoethyl)-4-(4-fluorophenyl)-3-isoxazolecarboxamide hydrochloride (5:6) ° 0.3 mol H20 in 30% yield, melting point 237°–239° (from ethanol).

The carbamates used as starting materials were prepared as follows:

From ethyl 4-(2-chlorophenyl)-3-isoxazolecarboxylate and t-butyl 2-(aminoethyl)carbamate the t-butyl [2-[4-(2-chlorophenyl)-3-isoxazolecarboxamido]ethyl]carbamate in 87% yield, melting point 132°–133° (from ethyl acetate/hexane);

from ethyl 4-(3-chlorophenyl)-3-isoxazolecarboxylate and t-butyl (2-aminoethyl)carbamate the t-butyl [2-[4-(3-chlorophenyl)-3-isoxazolecarboxamido]ethyl]carbamate in 78 6% yield, melting point 147°–148° (from ethyl acetate/hexane);

from ethyl 4-(4-chlorophenyl)-3-isoxazolecarboxylate and t-butyl (2-aminoethyl)carbamate the t-butyl [2-[4-(4-chlorophenyl)-3-isoxazolecarboxamido]ethyl]carbamate in 87% yield, melting point 135°–137° (from ethyl acetate/hexane);

from ethyl 4-(3-fluorophenyl)-3-isoxazolecarboxylate and t-butyl (2-aminoethyl)carbamate the t-butyl [2-[4-(3-fluorophenyl)-3-isoxazolecarboxamido]ethyl]carbamate in 75% yield, melting point 162°–163° (from ethanol/diethyl ether); and from ethyl 4-(4-fluorophenyl)-3-isoxazolecarboxylate and t-butyl (2-aminoethyl)carbamate the t-butyl [2-[4-(4-fluorophenyl)-3-isoxazolecarboxamido]ethyl]carbamate in 95 9% yield, melting point 140°-141° (from ethyl acetate/hexane).

The substituted ethyl 3-isoxazolecarboxylates used as starting materials were obtained from the corresponding substituted 5-amino-3-isoxazolecarboxylic acid esters which, in turn, were obtained from the corresponding β-cyano-α-oxo-dihydrocinnamic acid esters:
Ethyl 4-(2-chlorophenyl)-3-isoxazolecarboxylate in 52% yield as a red oil;
ethyl 4-(3-chlorophenyl)-3-isoxazolecarboxylate in 73% yield as a red oil;
ethyl 4-(4-chlorophenyl)-3-isoxazolecarboxylate in 51% yield as an orange oil;
ethyl 4-(3-fluorophenyl)-3-isoxazolecarboxylate in 65% yield as a yellow oil;
ethyl 4-(4-fluorophenyl)-3-isoxazolecarboxylate in 42% yield, melting point 57°-58° (from ethyl acetate/hexane); ethyl 5-amino-4-(2-chlorophenyl)-3-isoxazolecarboxylate in 76% yield, melting point 141°-142° (from ethyl acetate/hexane);
ethyl 5-amino-4-(3-chlorophenyl)-3-isoxazolecarboxylate in 22% yield, melting point 151°-152° (from ethyl acetate/hexane);
ethyl 5-amino-4-(4-chlorophenyl)-3-isoxazolecarboxylate in 52% yield, melting point 132°-133° (from ethyl acetate/hexane);
ethyl 5-amino-4-(3-fluorophenyl)-3-isoxazolecarboxylate in 75% yield, melting point 119° (from ethyl acetate/hexane); and
ethyl 5-amino-4-(4-fluorophenyl)-3-isoxazolecarboxylate in 75% yield, melting point 137°-138° (from ethyl acetate/hexane).

The dihydrocinnamic acid esters used as starting materials were prepared from the corresponding benzyl cyanides, sodium ethylate and diethyl oxalate according to the procedure described in Org. Synth. Coll. Vol. II (1943) 287 and Chem. Ber. 107 (1974) 2794-2795:
Ethyl 2-chloro-β-cyano-α-oxo-dihydrocinnamate in 67% 30 yield, melting point 133°-135° (from ethanol/water);
ethyl 3-chloro-β-cyano-α-oxo-dihydrocinnamate in 90% yield, melting point 76°-77° (from ethanol/water);
ethyl 4-chloro-H-cyano-α-oxo-dihydrocinnamate in 89.5% yield, melting point 137-139° (from water);
ethyl 2-fluoro-β-cyano-α-oxo-dihydrocinnamate in 85% yield, melting point 94°-95° (from ethanol/water); and
ethyl 4-fluoro-β-cyano-α-oxo-dihydrocinnamate in 90% yield, melting point 142°-144° (from ethanol/water).

EXAMPLE 16

5 0 g (15.1 mmol) of t-butyl 12-(4-phenyl-3-pyrazoleoarboxamido)ethyl]carbamate were stirred at room temperature for 16 hours with 6 ml (78.4 mmol) of trifluoroacetic acid and 10 ml of methylene chloride and thereafter evaporated under reduced pressure. The residue was treated with 7 ml of ethanolic hydrochloric acid (17.5% w/v) and evaporated. Recrystallization of the residue from methanol yielded 3.1 g (76.8%) of N-(2-aminoethyl)-4-phenyl-3-pyrazolecarboxamide hydrochloride as white crystals, melting point 285°-286°.

The t-butyl [2-(4-phenyl-3-pyrazolecarboxamido)ethyl]carbamate used as the starting material was prepared as follows:
(A) Benzaldehyde, N,N-dimethylglycine ethyl ester and sodium hydride were reacted in ether with the addition of a catalytic amount of ethanol according to the method described in Lieb. Ann. Chem. 703 (1967) 37°-43 to give ethyl α-dimethylaminocinnamate. This compound was then reacted according to the method described in Tetrahedron Letters, 46, (1978) 4573°-4574 with oxalyl chloride and hydrazine in 60% yield to give ethyl 4-phenyl-3-pyrazolecarboxylate, melting point 164°-165° after recrystallization from ethanol/diethyl ether.

The following 3-pyrazolecarboxylic acid esters were prepared in an analogous manner to that described above; for the preparation of the 1-methyl substituted compounds N-methylhydrazine was used in place of hydrazine, whereby in each case the resulting mixtures of the 1- and 2-methyl derivatives were separated by chromatography on silica gel with methylene chloride:
Ethyl 4-(3-fluorophenyl)-3-pyrazolecarboxylate in 46% yield, melting point 161°-162° (from ethanol/diethyl ether);
ethyl 4-(4-fluorophenyl)-3-pyrazolecarboxylate in 33.7% yield, melting point 177°-179° (from ethanol/diethyl ester);
ethyl 1-methyl-4-phenyl-3-pyrazolecarboxylate in 27% yield, melting point 92° (from ethyl acetate/hexane);
ethyl 4-(3-fluorophenyl)-1-methyl-3-pyrazolecarboxylate in 20% yield, melting point 93°-94° (from ethyl acetate/hexane): and
ethyl 4-(4-fluorophenyl)-1-methyl-3-pyrazolecarboxylate in 28% yield, melting point 58°-59° (from diethyl ether/petroleum ether).

(B) 5.0 g (23.12 mmol) of ethyl 4-phenyl-3-pyrazolecarboxylate were heated to 120° under reduced pressure for hours with 7.4 g (46.19 mmol) of t-butyl (2-aminoethyl)carbamate, whereby the ethanol formed was distilled off continuously. The reaction mixture was then taken up in methylene chloride and chromatographed on 150 g of silica gel with a 9:1, 8:2 and 7:3 mixture of methylene chloride and ethyl acetate as the eluting agent. The fractions which were pure according to the thin-layer chromatogram were combined and evaporated, and the residue was crystallized from ethyl acetate/hexane, whereby there were obtained 5.1 g (66.8%) of t-butyl [2-(4-phenyl-pyrazole-3carboxamido)ethyl]carbamate as white crystals, melting point 71°/162°-163° (still containing 0.05 mol of hexane).

EXAMPLE 17

4.4 g (12.63 mmol) of t-butyl [2-(4-(3-fluorophenyl)-3-pyrazolecarboxamido)ethyl]carbamate were stirred at room temperature for 16 hours with trifluoroacetic acid in an analogous manner to that in Example 16. Thereafter, the reaction mixture was evaporated and the residue was converted into the hydrochloride which was recrystallized from methanol/diethyl ether. After drying there were obtained 2.7 g (75%) of N-(2-aminoethyl)-4-(3-fluorophenyl)-3-pyrazolecarboxamide hydrochloride as white crystals, melting point 284°-285°.

The t-butyl [2-(4-(3-fluorophenyl)-3-pyrazolecarboxamido)ethyl]carbamate used as the starting material was prepared as follows:

4.6 q (19.64 mmol) of ethyl 4-(3-fluorophenyl)-3-pyrazolecarboxylate were reacted with t-butyl (2-aminoethyl)carbamate in an analoqous manner to that described in Example 16. Chromatoqraphy of the crude product and recrystallization from ethyl acetate/hexane yielded 4.4 g (64.6%) of t-butyl [2-(4-(3-fluorophenyl)-3-pyrazolecarboxamido)ethyl]carbamate as white crystals, melting point 175°–176°.

EXAMPLE 18

In an analogous manner to that described in Examples 16 and 17, from 6.4 g (18.37 mmol) of t-butyl [2-(4-(4-fluorophenyl)-3-pyrazolecarboxamido)ethyl]carbamate there were obtained after cleavage of the t-butoxycarbonyl group with trifluoroacetic acid and working-up 6.2 g of the desired hydrochloride as the crude product. Recrystallization from methanol/ether yielded 4.2 g (80%) of N-(2-aminoethyl)-4-(4-fluorophenyl)-3-pyrazolecarboxamide hydrochloride as white crystals, melting point 271°–273°.

The t-butyl [2-(4-(4-fluorophenyl)-3-pyrazolecarboxamido)ethyl]carbamate used as the starting material was prepared as follows:

In an analogous manner to that described in Examples 16 and 17, from 6.1 g (26 mmol) of ethyl 4-(4-fluorophenyl)-3-pyrazolecarboxylate there were obtained 6.4 g (67.2%) of t-butyl [2-(4-(4-fluorophenyl)-3-pyrazolecarboxamido)ethyl]carbamate as white crystals which melt at 162°–163° after recrystallization from ethyl acetate/hexane.

EXAMPLE 19

In an analoqous manner to that described in Examples 16 and 17, from 4.6 g (13.4 mmol) of t-butyl [2-(1-methyl-4-phenyl-3-pyrazolecarboxamido)ethyl]carbamate there were obtained, after cleavage of the t-butoxycarbonyl group with trifluoroacetic acid and working-up, 4.8 g of the crude hydrochloride. Recrystallization from ethanol/diethyl ether yielded 3.4 g (90%) of N-(2-aminoethyl)-1-methyl-4-phenyl-3-pyrazolecarboxamide hydrochloride as white crystals, melting point 182°.

The t-butyl [2-(1-methyl-4-phenyl-3-pyrazolecarboxamido)ethyl]carbamate used as the starting material was prepared as follows:

In an analogous manner to that described in Examples 16 and 17. from 6.6 g (28.7 mmol) of ethyl 1-methyl-4-phenyl-3-pyrazolecarboxylate there were obtained 4.6 g 71.5%) of t-butyl [2-(1-methyl-4-phenyl-3-pyrazolecarboxamido)ethyl]carbamate as white crystals, melting point 145° (from ethyl acetate/hexane).

EXAMPLE 20

3.4 g (9.38 mmol) of I-butyl [2-[4-(3-fluorophenyl)-1-methyl-3-pyrazolecarboxamido]ethyl]carbamate were stirred at room temperature with trifluoroacetic acid for 16 hours in an analogous manner to that described in Example 16. The reaction mixture was thereafter evaporated and the residue was converted into the hydrochloride. Recrystallization from ethanol/diethyl ether yielded 2.6 g (92.8%) pyrazolecarboxamide hydrochloride as white crystals. melting point 160°–161°.

The t-butyl [2-[4-(3-fluorophenyl)-1-methyl-3-pyrazolecarboxamido]ethyl]carbamate used as the starting material was prepared as follows:

3.4 g (13.7 mmol) of ethyl 4-(3-fluorophenyl)-1-methyl-3-pyrazolecarboxylate and 5.5 g (34.32 mmol) of t-butyl (2-aminoethyl)carbamate were stirred under reduced pressure for 18 hours at 130° and subsequently chromatographed on 100 g of silica gel. Elution with a 9:1, 8:2 and 7:3 mixture of methylene chloride and ethyl acetate yields 3.9 g of crystals which were recrystallized from ethyl acetate/hexane. In this manner there were obtained 3.4 g (68.5%) of t-butyl [2-[4-(3-fluorophenyl)-1-methyl-3-pyrazolecarboxamido]ethyl]carbamate as white crystals, melting point 124°.

EXAMPLE 21

9.8 g (27.0 mmol) of t-butyl [2-[4-(4-fluorophenyl)-1-methyl-3-pyrazolecarboxamido]ethyl]carbamate were stirred with trifluoroacetic acid at room temperature for 16 hours in an analogous manner to that described in Example 16. Thereafter, the reaction mixture was evaporated and the residue was converted into the hydrochloride. Recrystallization from ethanol/diethyl ether yielded 7.5 g (92.8%) of N-(2-aminoethyl)-4-(4-fluorophenyl)-1-methyl-3-pyrazolecarboxamide hydrochloride as white crystals, melting point 195°–196°.

The t-butyl [2-[4-(4-fluorophenyl)-1-methyl-3-pyrazolecarboxamido]ethyl]carbamate used as the starting material was prepared as follows:

8.6 g (34.6 mmol) of ethyl 4-(4-fluorophenyl)-1-methyl-3-pyrazolecarboxylate were heated to 70° for 60 minutes with 90 ml of 2N sodium hydroxide solution and 50 ml of water. Conversion into the acid form and recrystallization of the crude product from ethyl acetate/hexane yielded 6.9 g (gO 4%) of 4-(4-fluorophenyl)-1-methyl-3-pyrazolecarboxylic acid as white crystals, melting point 146°–147°.

6.9 g (31.34 mmol) of 4-(4-fluorophenyl)-1-methyl-3-pyrazolecarboxylic acid were heated to reflux for 2 hours with 400 ml of tetrahydrofuran and 5.2 g (32 mmol) of 1.1'-carbonyldiimidazole. Thereafter, 5.3 g (33 mmol) of t-butyl (2-aminoethyl)carbamate were added. The reaction mixture was heated to reflux for a further 2 hours and thereafter evaporated. The residue was partitioned between ethyl acetate and water, the organic phase was washed several times with water, dried over magnesium sulfate and evaporated. Recrystallization of the crystalline residue from ethyl acetate/hexane yielded 9.8 g (86.3%) of t-butyl 2-[4-(4-fluorophenyl)-1-methyl-3-pyrazolecarboxamido]ethyl]carbamate as white crystals, melting point 44°.

EXAMPLE 22

In an analoqous manner to that described in Example 1 from 7.2 g (18.78 mmol) of t-butyl [2-[5-(3,5-difluorophenyl)-4-thiazolecarboxamido]ethyl]carbamate there were obtained 5.7 g (95%) of N-(2-aminoethyl)-5-(3,5-difluorophenyl)-4-thiazolecarboxamide hydrochloride as white crystals, melting point 266°–267° (from methanol).

The t-butyl [2-[5-(3,5-difluorophenyl)-4-thiazolecarboxamido]ethyl]carbamate used as the starting material was prepared as follows:

25.0 g (179.7 mmol) of 3,5-difluorobenzonitrile were dissolved in 250 ml of ethanol and cooled to -10°. Thereafter, hydrochloric acid gas was conducted in during 20 minutes, whereby the internal temperature rose to 30°. The mixture was thereafter stirred at room temperature for 1 hour and nitrogen was conducted through the reaction mixture for 30 minutes in order to remove excess hydrochloric acid. The mixture was cooled to 0° and 200 ml of ether were added thereto. The turbid solution was left to stand at about 0° for 5 days and thereafter the crystals were filtered off. After drying at 50° in a vacuum there were obtained 27.8 g (70%) of 3,5-difluorobenzimino ethyl ether hydrochloride as white crystals of melting point 133°–134°.

300 ml of pyridine were cooled to 0°–5°. 5°–10 g of hydrogen sulfide were conducted in, then 27.5 g (124 mmol) of 3,5-difluorobenzimino ethyl ether hydrochloride were added thereto and the reaction mixture was left to stand closed at room temperature for about 48 hours. The excess hydrogen sulfide was removed by flushing with nitrogen and the reaction mixture was then concentrated in a vacuum. The residue was treated with 500 ml of hexane while stirring, whereupon the mixture was cooled to 5°. After 30minutes insoluble constituents were filtered off under suction. The yellow, clear solution was concentrated in a vacuum. There were obtained as the residue 23.8 g (95%) of o-ethyl 3,5-difluorothiobenzoate as an orange evil-smelling oil.

As described in Example 1(C). from o-ethyl 3,5-difluorothiobenzoate there was obtained in 82% yield ethyl 5-(3.5-difluorophenyl)-4-thiazolecarboxylate which melted at 112°–113° after recrystallization from ethyl acetate/hexane.

The ethyl 5-(3,5-difluorophenyl)-4-thiazolecarboxylate was saponified in an analogous manner to that described in Example 1(D). whereby after acidification there was obtained 5-(3,5-difluorophenyl)-4-thiazolecarboxylic acid in 97% yield, melting point 200° (from water).

In an analogous manner to that described in Example 1(E). from 5-(3,5-difluorophenyl)-4-thiazolecarboxylic acid there was obtained in 88% yield t-butyl [2-[5-(3,5-difluorophenyl)-4-thiazolecarboxamido]ethyl]-carbamate as white crystals of melting point 141°–142°.

EXAMPLE 23

(A) 6.3 g (13.3 mmol) of t-butyl [2-[5-(3-iodophenyl)-4-thiazolecarboxamido]ethyl]carbamate were dissolved in 70 ml of methylene chloride, treated with 5.1 ml of trifluoroacetic acid and stirred under reflux for 2 hours. Subsequently, the mixture was concentrated under reduced pressure. The residue was dissolved in 50 ml of methanol and treated with 5.2 ml of 2.7N ethanolic hydrochloric acid, whereby 4.8 g (88%) of N-(2-aminoethyl)-5-(3-iodophenyl)-4-thiazolecarboxamide hydrochloride were obtained as white crystals, melting point 272°–273°.

The t-butyl [2-[5-(3-iodophenyl)-4-thiazolecarboxamido]ethyl]carbamate used as the starting material was prepared as follows:

(B) 52.5 g (0.2 mol) of methyl 3-iodobenzoate were heated to reflux for 18 hours with 81 g (0.2 mol) of Lawesson reagent in 330 ml of xylene. By working-up in an analogous manner to that described in Example 1(B) there were obtained 47 g (84.4%) of O-methyl 3-iodothiobenzoate as a yellow evil-smelling oil which was used without further purification.

(C) Analogously to the method described in Synthesis 10, (1976), 681–682, 47 g (169 mmol) of O-methyl 3-iodothiobenzoate were reacted with ethyl isocyanoacetate in the presence of 1–5% powdered potassium hydroxide in ethanol. Recrystallization from ether yielded 45.8 g (75.4%) of ethyl 5-(3-iodophenyl)-4-thiazolecarboxylate as ochre crystals, melting point 77°–78°.

(D) 20 g (55.68 mmol) of ethyl 5-(3-iodophenyl)-4-thiazolecarboxylate were hydrolyzed in an analogous manner to that described in Example 1(D). whereby 17.6 g (95.5%) of 5-(3-iodophenyl)-4-thiazolecarboxylic acid were obtained as yellow crystals, melting point 186°.

(E) Reaction of 5.0 g (15.1 mmol) of 5-(3-iodophenyl)-4-thiazolecarboxylic acid with 2.6 g (16.2 mmol) of t-butyl (2-aminoethyl)carbamate in an analogous manner to that described in Example 1(E) yielded 6.3 g (88.1%) of t-butyl [2-[5-(3-iodophenyl)-4-thiazolecarboxamido]ethyl]carbamate as white crystals, melting point 111°–112°.

EXAMPLE A

Coated tablets of the following composition may be prepared in a manner known per se according to methods which are familiar to a person skilled in the art:

| Nucleus | |
| --- | --- |
| N-(2-Aminoethyl)-5-phenyl-4-thiazole-carboxamide hydrochloride | 100.00 mg |
| Powdered lactose | 148.00 mg |
| Maize starch | 120.00 mg |
| Polyvinylpyrrolidone | 20.00 mg |
| Sodium carboxymethylstarch | 10.00 mg |
| Magnesium stearate | 2.00 mg |
| Nucleus weight | 400.00 mg |

Procedure

The finely milled active substance is mixed with powdered lactose and maize starch. The mixture is moistened with an aqueous solution of polyvinylpyrrolidone and kneaded and the resulting mass is granulated, dried and sieved. The granulate is mixed with sodium carboxymethylstarch and magnesium stearate and pressed to tablets of suitable size.

| Coating layer | |
| --- | --- |
| Hydroxypropylmethylcellulose | 5.00 mg |
| Talc | 3.76 mg |
| Titanium dioxide | 1.00 mg |
| Yellow iron oxide | 0.20 mg |
| Sienna iron oxide | 0.04 mg |
| Total weight of a coated tablet | 410.00 mg |

Coating

Dissolve hydroxypropylmethylcellulose in demineralized water. Stir into this solution an aqueous suspension consisting of talc, titanium dioxide, yellow iron oxide and Sienna iron oxide. In a coating pan or a coating process unit, spray this film-coat suspension onto the tablets. The resulting film-coated tablets are then dried.

EXAMPLE B

Coated tablets of the following composition may be prepared in a manner known per se according to methods which are familiar to a person skilled in the art:

| | |
| --- | --- |
| N-(2-Aminoethyl)-5-phenyl-4-thiazole-carboxamide hydrochloride | 150.00 mg |
| Powdered lactose | 148.00 mg |
| Maize starch | 60.00 mg |
| Polyvinylpyrrolidone | 25.00 mg |
| Sodium carboxymethylstarch | 15.00 mg |
| Magnesium stearate | 2.50 mg |
| Nucleus weight | 400.00 mg |

Procedure

The finely milled active substance is mixed with powdered lactose and maize starch. The mixture is moistened with an aqueous solution of polyvinylpyrrolidone and kneaded and the resulting mass is granulated, dried and sieved. The granulate is mixed with sodium carboxymethylstarch and magnesium stearate and pressed to tablets of suitable size.

| Coating layer | |
|---|---|
| Hydroxypropylmethylcellulose | 4.50 mg |
| Ethylcellulose | 1.50 mg |
| Polyethyleneglycol 6000 | 0.60 mg |
| Talc | 2.40 mg |
| Titanium dioxide | 2.90 mg |
| Yellow iron oxide | 0.10 mg |
| Total weight of a coated tablet | 412.00 mg |

Coating

Dissolve hydroxypropylmethylcellulose in demineralized water and add ethylcellulose in suspension and polyethyleneglycol 6000. Stir into this solution an aqueous suspension consisting of talc, titanium dioxide and yellow iron oxide. In a coating pan or a coating process unit, spray this film-coat suspension onto the tablets. The resulting film-coated tablets are then dried.

EXAMPLE C

Coated tablets can be prepared from the following, likewise preferred compounds in analogy to Examples A and B:

N-(2-Aminoethyl)-5-(2-fluorophenyl)-4-thiazolecarboxamide hydrochloride;
N-(2-aminoethyl)-5-(3-fluorophenyl)-4-thiazolecarboxamide hydrochloride;
N-(2-aminoethyl)-5-(4-fluorophenyl)-4-thiazolecarboxamide hydrochloride;
N-(2-aminoethyl)-5-(4-chlorophenyl)-4-oxazolecarboxamide hydrochloride;
N-(2-aminoethyl)-5-(2-furyl)-4-oxazolecarboxamide hydrochloride;
N-(2-aminoethyl)-5-(3,5-dichlorophenyl)-4-thiazolecarboxamide hydrochloride;
N-(2-aminoethyl)-5-(2,4-difluorophenyl)-4-thiazolecarboxamide hydrochloride; and
N-(2-aminoethyl)-5-(3,5-difluorophenyl)-4-thiazolecarboxamide hydrochloride.

We claim:

1. A compound comprising an ethylenediamine monoamide derivative of the formula $$R-CO-NH-CH_2-CH_2-NH_2 \qquad I$$

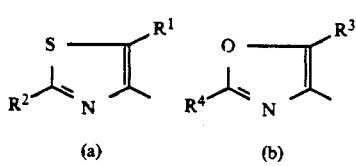

(a) and (b)

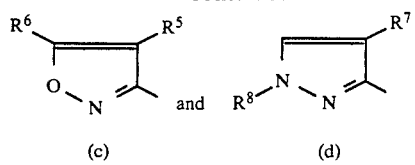

(c) and (d)

in which $R^1$ is phenyl, monohalophenyl, monolower-alkylphenyl, monolower-alkoxyphenyl, monotrifluoromethylphenyl, monocyanophenyl, dihalophenyl, furyl, thienyl, monohalothienyl or monophenyl-lower-alkoxyphenyl in which said monophenyl residue in unsubstituted or substituted with halogen, lower-alkyl, lower-alkoxy, nitro, cyano or hydroxy, $R^2$ is hydrogen, halogen or amino, $R^3$, $R^5$ and $R^7$ each are phenyl, monohalophenyl, dihalophenyl, thienyl, furyl or monohalofuryl, $R^4$ and $R^6$ each are hydrogen or amino and $R^8$ is hydrogen or lower-alkyl, or a pharmaceutically acceptable acid addition salt of the compound of formula I.

2. A compound according to claim 1, wherein R is group (a).

3. A compound according to claim 1, wherein R is group (b).

4. A compound according to claim 2, wherein $R^1$ is phenyl, monohalophenyl, monolower-alkylphenyl, monolower-alkoxyphenyl, monotrifluoromethylphenyl, monocyanophenyl, dihalophenyl, furyl, thienyl or monohlaothienyl, and $R^2$ is hydrogen or amino.

5. A compound according to claim 3, wherein $R^3$ is phenyl, monohalophenyl, dihalophenyl, thienyl, furyl or monohalofuryl, and $R^4$ is hydrogen.

6. A compound according to claim 4, wherein $R^1$ is phenyl, monohalophenyl or dihalophenyl, and $R^2$ is hydrogen.

7. A compound according to claim 5, wherein R phenyl, monohalophenyl or dihalophenyl, and $R^4$ is hydrogen.

8. The compound according to claim 4, N-(2-aminoethyl)-5-phenyl-4-thiazolecarboxamide.

9. The compound according to claim 4. N-(2-aminoethyl)-5-(3-fluorophenyl)-4-thiazolecarboxamide.

10. The compound according to claim 4, N-(2-aminoethyl)5-(3,5-difluorophenyl)-4- thiazolecarboxamide.

11. The compound according to claim 1,
N-(2-Aminoethyl)- 5-(2-fluorophenyl)-4-thiazolecarboxamide;
N-(2-aminoethyl)-5-(4-fluorophenyl)-4-thiazolecarboxamide;
N-(2-aminoethyl)-5-(4-chlorophenyl)-4-oxazolecarboxamide;
N-(2-aminoethyl)-5-(2-furyl)-4-oxazolecarboxamide;
N-(2-aminoethyl)-5-(3,5-dichlorophenyl)-4-thiazolecarboxamide;
N-(2-aminoethyl)-5-(2,4-difluorophenyl)-4-thiazolecarboxamide;
N-(2-aminoethyl)-5-(4-fluorophenyl)-4-oxazolecarboxamide;
N-(2-aminoethyl)-5-(4-bromophenyl)-4-oxazolecarboxamide;
N-(2-aminoethyl)-4-(3-fluorophenyl)-3-isoxazolecarboxamide and;
N-(2-aminoethyl)-4-(3-fluorophenyl)-1-methyl-3-pyrazolecarboxamide.

12. A composition for preventing and treating depressive states and cognitive disorders comprising: an effective amount of a monoamine oxidase inhibiting compound of the formula

R—CO—NH—CH$_2$—CH$_2$—NH$_2$   I wherein R is one of groups

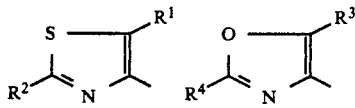

(a)  (b)

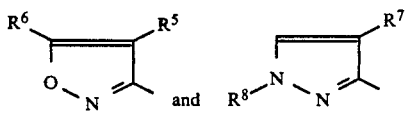

(c)  (d)

in which R$^1$ is phenyl, monohalophenyl, monolower-alkylphenyl, monolower-alkoxyphenyl, monotrifluoromethylphenyl, monocryanophenyl, dihalophenyl, furyl, thienyl, monohalothienyl or monophenyl-lower-alkoxyphenyl in which said monophenyl residue in unsubstituted or substituted with halogen, lower-alkyl, lower-alkoxy, nitro, cyano or hydroxy, R$^2$ is hydrogen, halogen or amino, R$^3$, R$^5$ and R$^7$ each are phenyl, monohalophenyl, dihalophenyl, thienyl, furyl or monohalofuryl, R$^4$ and R$^6$ each are hydrogen or amino and R$^8$ is hydrogen or lower-alkyl, or a pharmaceutically acceptable acid addition salt of the compound of formula I, and a pharmaceutically acceptable carrier material.

13. A method for treating depressive states and cognitive disorders in a patient in need of such treatment comprising: administering an effective amount of a monoamine oxidase inhibiting compound of the formula r—CO—NH—CH$_2$—CH$_2$—NH$_2$   I where R is one of groups

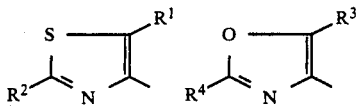

(a)  (b)

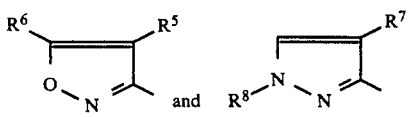

(c)  (d)

in which R$^1$ is phenyl, monohalophenyl, monolower-alkylphenyl, monolower-alkoxyphenyl, monotrifluoromethylphenyl, monocyanophenyl, dihalophenyl, furyl, thienyl, monohalothienyl or monophenyl-lower-alkoxyphenyl in which said monophenyl residue in unsubstituted or substituted with halogen, lower-alkyl, lower-alkoxy, nitro, cyano or hydroxy, R$^2$ is hydrogen, halogen or amino, R$^3$, R$^5$ and R$^7$ each are phenyl, monohalophenyl, dihalophenyl, thienyl, furyl or monohalofuryl, R$^4$ and R$^6$ each are hydrogen or amino and R$^8$ is hydrogen or lower-alkyl, or a pharmaceutically acceptable acid addition salt of the compound of formula I.

* * * * *

UNITED STATES PATENT AND TRADEMARK OFFICE
CERTIFICATE OF CORRECTION

PATENT NO. : 5,011,849
DATED : April 30, 1991
INVENTOR(S) : Walter Gassner, Rene Imhof and Emilio Kyburz It is certified that error appears in the above-identified patent and that said Letters Patent is hereby corrected as shown below:

In claim 4, column 38, line 32, change "monohlaothienyl" to -- monohalothienyl --.

In claim 7, column 38, line 39, after wherein, delete "R" and insert therefor -- $R^3$ is --.

In claim 12, column 39, line 26, change "monocryanophenyl" to -- monocyanophenyl --.

In claim 13, column 40, line 6, formula I should read
-- $R-CO-NH-CH_2-CH_2-NH_2$     I --.

Signed and Sealed this

Twenty-seventh Day of October, 1992

Attest:

DOUGLAS B. COMER

Attesting Officer    Acting Commissioner of Patents and Trademarks